(12) United States Patent
Akcan et al.

(10) Patent No.: US 11,911,510 B2
(45) Date of Patent: Feb. 27, 2024

(54) PHARMACEUTICAL DOSAGE FORMS

(71) Applicant: Purdue Pharma L.P., Stamford, CT (US)

(72) Inventors: Ozgur Akcan, Parlin, NJ (US); Richard Mannion, Furlong, PA (US)

(73) Assignee: Purdue Pharma L.P, Stamford, CT (US)

( * ) Notice: Subject to any disclaimer, the term of this patent is extended or adjusted under 35 U.S.C. 154(b) by 0 days.

(21) Appl. No.: 16/642,742

(22) PCT Filed: Aug. 30, 2018

(86) PCT No.: PCT/US2018/048904
§ 371 (c)(1),
(2) Date: Feb. 27, 2020

(87) PCT Pub. No.: WO2019/046611
PCT Pub. Date: Mar. 7, 2019

(65) Prior Publication Data
US 2021/0077409 A1    Mar. 18, 2021

Related U.S. Application Data

(60) Provisional application No. 62/552,521, filed on Aug. 31, 2017.

(51) Int. Cl.
*A61K 9/20* (2006.01)
*A61K 31/485* (2006.01)

(52) U.S. Cl.
CPC .......... *A61K 9/2031* (2013.01); *A61K 9/2013* (2013.01); *A61K 31/485* (2013.01)

(58) Field of Classification Search
None
See application file for complete search history.

(56) References Cited

U.S. PATENT DOCUMENTS 6,117,453 A     9/2000  Seth et al.
9,504,656 B2 *  11/2016 Vamvakas ............ A61K 9/4858
(Continued)

FOREIGN PATENT DOCUMENTS

JP      2010519201 A    6/2010
JP      2014510094 A    4/2014
(Continued)

OTHER PUBLICATIONS

Sodium dioctyl sulfosuccinate. Ataman Chemicals. https://atamankimya.com/sayfalaralfabe.asp?LanguageID=1&cid=3&id=2860&id2=8961. 17 pages.Jan. 21, 2022 (Year: 2022).*

(Continued)

*Primary Examiner* — Lakshmi S Channavajjala
(74) *Attorney, Agent, or Firm* — Lowenstein Sandler LLP

(57) ABSTRACT

The invention relates to a solid oral extended release pharmaceutical dosage form comprising an extended release matrix formulation. The extended release matrix formulation comprises (1) at least one active agent, (2) at least one anionic surfactant, and (3) at least about 40% by weight (based on the weight of the extended release matrix formulation) of at least one polyethylene oxide. In certain embodiments, the molar ratio of the at least one anionic surfactant to the at least one active agent is from about 1:2 to about 10:1.

12 Claims, 6 Drawing Sheets

(56) References Cited

U.S. PATENT DOCUMENTS

| | | | |
|---|---|---|---|
| 2005/0255157 A1 | 11/2005 | Sen | |
| 2006/0099256 A1 | 5/2006 | Price et al. | |
| 2007/0281016 A1 | 12/2007 | Kao et al. | |
| 2008/0075774 A1* | 3/2008 | Williams | A61K 33/00 424/468 |
| 2008/0152595 A1* | 6/2008 | Emigh | A61K 9/2059 424/10.4 |
| 2011/0275658 A1 | 11/2011 | Evenstad | |
| 2013/0171257 A1 | 7/2013 | Kumar et al. | |
| 2016/0030419 A1 | 2/2016 | Oshlack et al. | |

FOREIGN PATENT DOCUMENTS

| | | | |
|---|---|---|---|
| WO | 9945887 A2 | 9/1999 | |
| WO | WO-2008011595 A3 * | 1/2008 | A61K 9/2013 |
| WO | 2008100107 A1 | 8/2008 | |
| WO | 2009144286 A1 | 12/2009 | |
| WO | 2012131463 A2 | 10/2012 | |
| WO | 2017/070566 A1 | 4/2017 | |
| WO | 2017/136460 A1 | 8/2017 | |

OTHER PUBLICATIONS

International Search Report for International Application No. PCT/US2018/048904 dated Nov. 19, 2018, 3 pgs.

European Search Report of Application No. 18851393.1 dated Apr. 16, 2021, 3 pgs.

Anonymous, "Oxycodone Hydrochloride Extended-Release Tablets (IPC OXY)," Intellipharmaceutics Briefing Document, Jul. 26, 2017, pp. 1-53.

Maincent, et al., "Recent advances in abuse-deterrent technologies for the delivery of opioids," International Journal of Pharmaceutics, 2017, vol. 510, pp. 57-72, Elsevier.

Mastropietro et al., "Abuse-deterrent formulations: Part 2: commercial products and proprietary technologies," Expert Opinion on Pharmacotherapy, Nov. 25, 2014, pp. 1-19.

* cited by examiner

PHARMACEUTICAL DOSAGE FORMS

TECHNICAL FIELD OF THE INVENTION

The invention relates to solid oral pharmaceutical dosage forms providing an extended release of an active agent. In certain embodiments, the release rate of the active agent approximates zero order release kinetics. In certain embodiments, the dosage forms also exhibit abuse-deterrent properties.

BACKGROUND OF THE INVENTION

Pharmaceutical dosage forms which provide an extended release of the active agent are developed to enable control of drug exposure over time, and may increase patient compliance by reducing the frequency of administration. Out of the pharmaceutical dosage forms, extended release pharmaceutical dosage forms providing a zero-order release of the active agent, wherein the active agent is released at a constant rate, are of particular interest. After their administration and a subsequent initial rise in the plasma concentration, such dosage forms can achieve a relatively constant plasma concentration lying, with proper dosing, in the so-called therapeutic range, which is bounded below by a minimum effective concentration and above by a minimum toxic concentration.

Considerable efforts have been made to develop and manufacture pharmaceutical dosage forms providing a zero-order release of the active agent. The respective techniques are often complex and result in complex tablet structures. For example, certain tablets using OROS® (Osmotic Controlled Release Oral Delivery System) technology exhibit, in addition to one or more drug layers, a push layer, and a semipermeable membrane with one or more small laser drilled holes. It is thus desirable to develop alternative formulation technologies, which ideally allow a zero-order release profile to be obtained by simpler means.

Another challenge for formulation scientists is that pharmaceutical dosage forms containing active agents such as opioid analgesics sometimes are the subject of abuse. This is particularly the case for extended release dosage forms which contain a higher dose of the active agent, as compared to immediate-release products.

Opioid products can be abused in a number of ways. For example, they can be swallowed whole, crushed and swallowed, crushed and snorted, crushed and smoked, or crushed, dissolved and injected. Because opioid products are often manipulated for purposes of abuse by different routes of administration or to defeat extended-release properties, most abuse-deterrent technologies developed to date are intended to make manipulation more difficult or to make abuse of the manipulated products less attractive or less rewarding.

There continues to exist a need for pharmaceutical dosage forms which provide an extended release of the active agent, and in particular an extended release of the active agent which approximates zero order release kinetics, by simple means (including, e.g., easy manufacture of the dosage form), and which preferably also exhibit abuse-deterrent properties.

SUMMARY OF THE INVENTION

In certain embodiments, the invention is directed to a solid oral pharmaceutical dosage form which provides an extended release of the active agent contained therein.

In certain embodiments, the invention is directed to a solid oral extended release pharmaceutical dosage form, which provides a substantially zero-order release of the active agent contained therein, for example, over a time period of at least 4 hours, e.g., from 4 hours to 8 hours of dissolution.

In certain embodiments, the invention is directed to a solid oral extended release pharmaceutical dosage form having abuse-deterrent properties.

In certain embodiments, the invention is directed to a solid oral extended release pharmaceutical dosage form, which is subject to less intranasal abuse than other dosage forms.

In certain embodiments, the invention is directed to a solid oral extended release pharmaceutical dosage form, which exhibits features impeding the crushing or pulverization of the dosage form.

In certain embodiments, the invention is directed to a solid oral extended release pharmaceutical dosage form comprising an extended release matrix formulation, the extended release matrix formulation comprising:
(1) at least one active agent;
(2) at least one anionic surfactant; and
(3) at least about 40% by weight (based on the weight of the extended release matrix formulation) of at least one polyethylene oxide.

In certain such embodiments, the molar ratio of the at least one anionic surfactant to the at least one active agent is from about 1:2 to about 10:1. In certain embodiments, the at least one active agent is a salt of an active agent comprising a cationic active agent molecule and at least one anionic counterion. It is understood that the at least one active agent contained in said solid oral extended release pharmaceutical dosage form is present in a pharmaceutically effective amount.

In certain embodiments, the invention is directed to a process of preparing a solid oral extended release pharmaceutical dosage form, comprising the steps of
(a) combining at least
(1) at least one active agent;
(2) at least one anionic surfactant; and
(3) at least about 40% by weight (based on the weight of the extended release matrix formulation) of at least one polyethylene oxide;
to form a composition;
(b) shaping the composition to form an extended release matrix formulation; and
(c) optionally curing said extended release matrix formulation comprising at least a curing step of subjecting the extended release matrix formulation to a temperature which is at least the softening temperature of said polyethylene oxide for a time period of at least about 1 minute.

In certain embodiments, the molar ratio of the at least one anionic surfactant to the at least one active agent is from about 1:2 to about 10:1.

In certain embodiments, the invention is directed to a solid oral extended release pharmaceutical dosage form as disclosed herein, for use in a method of treating or preventing pain, wherein the solid oral extended release pharmaceutical dosage form contains a pharmaceutically effective amount of at least one active agent. In certain embodiments, the at least one active agent comprises an opioid agonist that is present in an amount to provide analgesic effects.

In certain embodiments, the invention is directed to a method of treating or preventing pain comprising administering to a patient identified in need thereof a solid oral extended release pharmaceutical dosage form as disclosed herein, wherein the solid oral extended release pharmaceutical dosage form comprises an analgesically effective amount of an opioid agonist.

In certain embodiments, the invention is directed to the use of an extended release matrix formulation comprising:
(1) at least one active agent;
(2) at least one anionic surfactant; and
(3) at least about 40% by weight (based on the weight of the extended release matrix formulation) of at least one polyethylene oxide;
in a solid oral extended release pharmaceutical dosage form, for achieving a substantially zero order release of the at least one active agent from said pharmaceutical dosage form. In certain such embodiments, the molar ratio of the at least one anionic surfactant to the at least one active agent is from about 1:2 to about 10:1.

In certain embodiments, the invention is directed to the use of an extended release matrix formulation comprising:
(1) at least one active agent;
(2) at least one anionic surfactant; and
(3) at least about 40% by weight (based on the weight of the extended release matrix formulation) of at least one polyethylene oxide;
in a solid oral extended release pharmaceutical dosage form, for achieving an in vitro dissolution rate of the dosage form with
an amount of the at least one active agent released at x hours, wherein x is an integer selected from a number between 2 and 12; and
an amount of the at least one active agent released at y hours, wherein y is an integer selected from a number between 6 and 24, and y≥x+4;
which complies at least for one combination of x and y with equations (I) and (II):

$$\text{the amount released at } y \text{ hours} \leq \left(\frac{y}{x} \times \text{amount released at } x \text{ hours}\right) \times 1.25 \quad (I)$$

$$\text{the amount released at } y \text{ hours} \geq \left(\frac{y}{x} \times \text{amount released at } x \text{ hours}\right) \times 0.75, \quad (II)$$

when the dosage form is subjected to an in-vitro dissolution test in a USP Apparatus 1 (basket) at 100 rpm in 900 ml simulated gastric fluid without enzymes (SGF) at 37.0±0.5° C. In certain such embodiments, the molar ratio of the at least one anionic surfactant to the at least one active agent is from about 1:2 to about 10:1.

In certain embodiments, the invention is directed to a method of achieving a substantially zero order release of at least one active agent from a solid oral extended release pharmaceutical dosage form, comprising a) providing said pharmaceutical dosage form to a subject in need thereof; or b) subjecting said pharmaceutical dosage form to an in-vitro dissolution test in a USP Apparatus 1 (basket) at 100 rpm in 900 ml simulated gastric fluid without enzymes (SGF) at 37.0±0.5° C.; wherein said pharmaceutical dosage form comprises an extended release matrix formulation comprising:
(1) said at least one active agent;
(2) at least one anionic surfactant; and
(3) at least about 40% by weight (based on the weight of the extended release matrix formulation) of at least one polyethylene oxide.

In certain such embodiments, the molar ratio of the at least one anionic surfactant to the at least one active agent is from about 1:2 to about 10:1.

In certain embodiments, the invention is directed to a method of achieving an in-vitro dissolution rate of at least one active agent from a solid oral extended release pharmaceutical dosage form with
an amount of the at least one active agent released at x hours, wherein x is an integer selected from a number between 2 and 12; and
an amount of the at least one active agent released at y hours, wherein y is an integer selected from a number between 6 and 24, and y≥x+4;
wherein the dissolution rate complies at least for one combination of x and y with equations (I) and (II):

$$\text{the amount released at } y \text{ hours} \leq \left(\frac{y}{x} \times \text{amount released at } x \text{ hours}\right) \times 1.25 \quad (I)$$

$$\text{the amount released at } y \text{ hours} \geq \left(\frac{y}{x} \times \text{amount released at } x \text{ hours}\right) \times 0.75, \quad (II)$$

said method comprising subjecting said pharmaceutical dosage form to an in-vitro dissolution test in a USP Apparatus 1 (basket) at 100 rpm in 900 ml simulated gastric fluid without enzymes (SGF) at 37.0±0.5° C.,
wherein said pharmaceutical dosage form comprises an extended release matrix formulation comprising:
(1) said at least one active agent;
(2) at least one anionic surfactant; and
(3) at least about 40% by weight (based on the weight of the extended release matrix formulation) of at least one polyethylene oxide.

In certain embodiments, the molar ratio of the at least one anionic surfactant to the at least one active agent is from about 1:2 to about 10:1.

In describing the invention, the following terms are to be used as indicated below.

As used herein, the singular forms "a", "an", and "the" include plural references unless the context clearly indicates otherwise.

The term "abuse" is defined for purposes of the invention as the intentional, non-therapeutic use of a drug product or substance, even once, to achieve a desirable psychological or physiological effect.

The term "abuse-deterrent properties" is defined for purposes of the invention as those properties shown to meaningfully deter abuse, even if they do not fully prevent abuse.

The term "extended release" is defined for purposes of the invention as to refer to products which are formulated to make the drug available over an extended period after ingestion, thereby allowing a reduction in dosing frequency compared to a drug presented as a conventional dosage form (e.g., as a solution or an immediate release dosage form).

The term "immediate release" is defined for purposes of the invention as to refer to products which are formulated to allow the drug to dissolve in the gastrointestinal contents with no intention of delaying or prolonging the dissolution or absorption of the drug. In certain embodiments, the term "immediate release" dosage form refers to a dosage form releasing at least about 70% of the active agent within 45 minutes, as measured by in-vitro dissolution in a USP Apparatus 1 (basket) at 100 rpm in 900 ml simulated gastric fluid without enzymes (SGF) at 37.0±0.5° C.

The term "simulated gastric fluid" or "SGF" used herein refers to an aqueous solution utilized in dissolution testing to mimic the conditions of the stomach, e.g., a solution of 0.1 N HCl.

The term "USP Apparatus 1 (basket)" refers to the Apparatus 1 (Basket Apparatus) described in U.S. Pharmacopoeia 39 (2016) (see, in particular, Section <711> Dissolution). The term "in-vitro dissolution test in a USP Apparatus 1 (basket)" refers to the respective method using the Apparatus 1 (basket) as described in U.S. Pharmacopoeia 39 (2016) (see, in particular Section <711> Dissolution).

For purposes of the invention, the "in-vitro dissolution test in a USP Apparatus 1 (basket)" is used in a slightly modified form, by equipping the USP Apparatus 1 basket with a retaining spring placed in the upper part of the basket (above the tablet), to reduce the propensity of the polyethylene oxide containing tablets, once hydrated in the dissolution medium, to stick to the solid underside of the top of the basket or the base of the shaft. For example, a passivized stainless steel 316 spring, 1.5-cm outside diameter and 2-cm length can be used.

The term "zero-order release rate" refers to the rate of active agent release from a dosage form which is independent of remaining active agent concentration in the dosage form, such that the rate is relatively constant over a period of time. A dosage form exhibiting zero order release would exhibit a relatively straight line in a graphical representation of percent active agent released versus time.

In certain embodiments of the invention, "substantially zero order release" is defined as referring to a dosage form which, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released at x hours, wherein x is an integer selected from a number between 2 and 12; and an amount of the at least one active agent released at y hours, wherein y is an integer selected from a number between 6 and 24, and y≥x+4;

which complies at least for one combination of x and y with equations (I) and (II):

$$\text{the amount released at } y \text{ hours} \leq \left(\frac{y}{x} \times \text{amount released at } x \text{ hours}\right) \times 1.25 \quad (I)$$

$$\text{the amount released at } y \text{ hours} \geq \left(\frac{y}{x} \times \text{amount released at } x \text{ hours}\right) \times 0.75 \quad (II)$$

The expression "at least for one combination of x and y" means that a dissolution rate has to comply with the equations (I) and (II) only for one combination of x and y, in order to be considered a "substantially zero order release" rate according to the above definition. For example, a dosage form which releases under the conditions specified above an amount of active agent at 4 hours of 20%, and an amount of active agent at 8 hours which lies between 30% and 50% (the limits are calculated by multiplying the exactly proportional value of 40% with the factor 0.75 and 1.25, respectively) would meet the above definition of "substantially zero order release", since its dissolution rate complies with the equations (I) and (II) at least for the combination wherein x=4 and y=8. For purposes of the invention, such a dosage form can be described to provide "a substantially zero order release from 4 to 8 hours". Another (or the same) dosage form, which releases under the conditions specified above an amount of active agent at 8 hours of 40%, and an amount of active agent at 12 hours which lies between 45% and 75%, would likewise meet the above definition of "substantially zero order release", since it complies with the equations (I) and (II) at least for the combination wherein x=8 and y=12. For purposes of the invention, such a dosage form can be described to provide a "substantially zero order release from 8 to 12 hours". Thus, in order to assess whether a dosage form provides a substantially zero order release, e.g. within a time period of from 4 to 8 hours (x=4 and y=8), it is only necessary to consider the pair of % released values at the endpoints of the respective time period (in the example given, the % released values at 4 hours and 8 hours), although the definition does not preclude that other pairs of % released values lying within that time period (in the exemplified time period of 4 to 8 hours, for example the % released values at 4 hours and 6 hours) may be proportional as well.

The term "solid oral extended release pharmaceutical dosage form" refers to the administration form comprising a unit dose of active agent in extended release form such as an "extended release matrix formulation" and optionally other adjuvants and additives conventional in the art, such as a protective coating or a capsule and the like, and optionally any other additional features or components that are used in the dosage form. The extended release pharmaceutical dosage form can be, for instance, a tablet comprising the extended release matrix formulation, or a capsule comprising the extended release matrix formulation in the form of multi particulates. The "extended release pharmaceutical dosage form" may comprise a portion of the active agent in extended release form and another portion of the active agent in immediate release form, e.g., as an immediate release layer of the active agent surrounding the dosage form or an immediate release component included within the dosage form. In certain embodiments, a "solid oral extended release pharmaceutical dosage form" according to the invention can be provided once daily or twice daily in a dosing regimen.

The "solid oral extended release pharmaceutical dosage form" can comprise one or more extended release matrix formulations. If there is more than one extended release matrix formulation, they can be identical (e.g., in the case of extended release matrix formulations in the form of multi particulates), or different (e.g., in the case of layered/"sandwich-type", or core-shell arrangements). For purposes of the invention, the term "solid oral extended release pharmaceutical dosage form" does not encompass dosage forms using OROS® (Osmotic Controlled Release Oral Delivery System) technology. Therefore the "solid oral extended release pharmaceutical dosage form" preferably excludes dosage forms that include a semipermeable coating. However, the "solid oral extended release pharmaceutical dosage form" can include for example a cosmetic film coating which is coated onto the extended release matrix formulation.

The term "extended release matrix formulation" is defined as a shaped solid form of a composition comprising at least one active agent (or active agent salt), at least one anionic surfactant, and at least one extended release feature such as an extended release matrix material, such as, polyethylene oxide. The at least one anionic surfactant, such as, at least one ($C_8$-$C_{18}$) alkyl sulfate (e.g., sodium lauryl sulfate), is present in the extended release matrix formulation in a releasable form (i.e., not in a sequestered form, such that the anionic surfactant is released, if the dosage form is taken as directed). The composition can optionally comprise more than these three compounds, namely further active agents and additional retardants and/or other materials, including but not limited to other adjuvants and additives conventional in the art, such as lubricants.

The term "surfactant" refers to an organic substance which has an amphiphilic structure (including a hydrophobic portion and a hydrophilic portion) and can lower the surface tension of the medium (e.g., water) in which it is dissolved, and/or the interfacial tension with other phases. A surfactant is further characterized by the capability to form micelles in aqueous phase, once the critical micellization concentration (CMC) is reached. Reference is made to Remington's Pharmaceutical Sciences, 18th edition, 1990, Chapter 19, pages 267-271, the contents of which are hereby incorporated in their entirety. In certain embodiments, the term "surfactant" refers to a substance which additionally has a molecular weight below 5000 g/mol. In certain such embodiments, the term "surfactant" refers to a substance which has a molecular weight below 1000 g/mol.

The term "anionic surfactant" refers to a surfactant, which dissociates in aqueous phase into an organic, negatively charged, surface-active ion (anion) and a counter-ion (cation). The most commonly used anionic surfactants are those containing carboxylate, sulfonate, and sulfate ions.

Examples of anionic surfactants include alkyl carboxylates and fatty acid salts, esters of fatty acids, alkyl ether carboxylates, alkyl sulfonates, alpha-olefin sulfonates, alkyl aryl sulfonates, sulfosuccinates, sulfonated fatty acid esters, ethoxylated alkyl sulfates, alkyl sulfates, fatty alcohol ether sulfates, acyl lactylates, N-acyl sarcosinates, alkyl carbonates, N-acyl glutamates, alkyl phosphates, and alkylether phosphates.

The term "alkyl" includes, unless expressly stated otherwise, branched and linear alkyl groups.

The term "polyethylene oxide" ("PEO") is defined as having an approximate molecular weight of at least 25,000, and preferably as having an approximate molecular weight of at least 100,000, measured as is conventional in the art, and preferably measured based on rheological measurements as described further below. Compositions with lower approximate molecular weight are usually referred to as polyethylene glycols.

For purposes of the invention, the approximate molecular weight of a polyethylene oxide is determined based on rheological measurements. Since polyethylene oxides are polydisperse polymers, the approximate molecular weight of a polyethylene oxide (determined based on rheological measurements) corresponds to an average molecular weight.

For purposes of the invention, a polyethylene oxide having a certain approximate molecular weight (determined based on rheological measurements) can be a single grade of a (commercially available) polyethylene oxide, or a mixture or blend of two or more grades.

The approximate molecular weight of a polyethylene oxide (single grade or mixture of grades), is determined based on rheological measurements, as follows:

Polyethylene oxide is considered to have an approximate molecular weight of 100,000 when a 5% (by weight) aqueous solution of said polyethylene oxide using a Brookfield viscometer Model RVT, spindle No. 1, at 50 rpm, at 25° C. shows a viscosity range of 30 to 50 mPa s (cP);

Polyethylene oxide is considered to have an approximate molecular weight of 300,000 when a 5% (by weight) aqueous solution of said polyethylene oxide using a Brookfield viscometer Model RVF, spindle No. 1, at 10 rpm, at 25° C. shows a viscosity range of 600 to 1,200 mPa s (cP);

Polyethylene oxide is considered to have an approximate molecular weight of 600,000 when a 5% (by weight) aqueous solution of said polyethylene oxide using a Brookfield viscometer Model RVF, spindle No. 2, at 2 rpm, at 25° C. shows a viscosity range of 4,500 to 8,800 mPa s (cP);

Polyethylene oxide is considered to have an approximate molecular weight of 900,000 when a 5% (by weight) aqueous solution of said polyethylene oxide using a Brookfield viscometer Model RVF, spindle No. 2, at 2 rpm, at 25° C. shows a viscosity range of 8,800 to 17,600 mPa s (cP);

Polyethylene oxide is considered to have an approximate molecular weight of 1,000,000 when a 2% (by weight) aqueous solution of said polyethylene oxide using a Brookfield viscometer Model RVF, spindle No. 1, at 10 rpm, at 25° C. shows a viscosity range of 400 to 800 mPa s (cP);

Polyethylene oxide is considered to have an approximate molecular weight of 2,000,000 when a 2% (by weight) aqueous solution of said polyethylene oxide using a Brookfield viscometer Model RVF, spindle No. 3, at 10 rpm, at 25° C. shows a viscosity range of 2,000 to 4,000 mPa s (cP);

Polyethylene oxide is considered to have an approximate molecular weight of 4,000,000 when a 1% (by weight) aqueous solution of said polyethylene oxide using a Brookfield viscometer Model RVF, spindle No. 2, at 2 rpm, at 25° C. shows a viscosity range of 1,650 to 5,500 mPa s (cP);

Polyethylene oxide is considered to have an approximate molecular weight of 5,000,000 when a 1% (by weight) aqueous solution of said polyethylene oxide using a Brookfield viscometer Model RVF, spindle No. 2, at 2 rpm, at 25° C. shows a viscosity range of 5,500 to 7,500 mPa s (cP);

Polyethylene oxide is considered to have an approximate molecular weight of 7,000,000 when a 1% (by weight) aqueous solution of said polyethylene oxide using a Brookfield viscometer Model RVF, spindle No. 2, at 2 rpm, at 25° C. shows a viscosity range of 7,500 to 10,000 mPa s (cP);

Polyethylene oxide is considered to have an approximate molecular weight of 8,000,000 when a 1% (by weight) aqueous solution of said polyethylene oxide using a Brookfield viscometer Model RVF, spindle No. 2, at 2 rpm, at 25° C. shows a viscosity range of 10,000 to 15,000 mPa s (cP).

In certain embodiments, in case the extended release matrix formulation contains two or more grades of polyethylene oxide, either the entire mixture of the polyethylene oxide grades contained therein, or a subgroup thereof (including only a single polyethylene oxide grade) can meet the definition of a given approximate molecular weight (or approximate molecular weight range), determined based on rheological measurements.

For purposes of the invention, a polyethylene oxide (single grade or mixture of grades) meeting two or more criteria of the above rheological tests, is assigned the respective higher approximate molecular weight. For example, a polyethylene oxide which, in a 1% (by weight) aqueous solution of said polyethylene oxide using a Brookfield viscometer Model RVF, spindle No. 2, at 2 rpm, at 25° C., shows a viscosity of 5,500 mPa s (cP), which is the threshold value between an approximate molecular weight of 4,000,000 and 5,000,000, would be assigned an approximate molecular weight of 5,000,000. Likewise, a polyethylene oxide (single grade or blend of grades) meeting the rheological test criteria for both an approximate molecular weight of 900,000 and of 1,000,000 (under the respective test conditions as specified above), would be assigned the higher approximate molecular weight of 1,000,000.

Similarly, the situation may arise that the viscosity measured for a polyethylene oxide (single grade or blend of grades) using the above rheological test conditions, falls within an herein "undefined" viscosity range, which is herein not assigned to a specific approximate molecular weight. For example, a polyethylene oxide might show a viscosity, which exceeds the viscosity range herein assigned to an approximate molecular weight of 1,000,000 (under the respective test conditions as specified above), and which, on the other hand, lies below the viscosity range herein assigned to an approximate molecular weight of 2,000,000 (under the respective test conditions as specified above). For purposes of the invention, such a polyethylene oxide would be assigned the approximate molecular weight which is associated with the viscosity range closest to the measured viscosity.

The term "direct compression" is defined for purposes of the invention as referring to a tableting process wherein a tablet or any other compressed dosage form is made by a process comprising the steps of dry blending the compounds and compressing the dry blend to form the dosage form, e.g., by using a diffusion blend and/or convection mixing process (e.g., Guidance for Industry, SUPAC-IR/MR: Immediate Release and Modified Release Solid Oral Dosage Forms, Manufacturing Equipment Addendum).

When conducting the breaking strength or tablet hardness test as described in Remington's Pharmaceutical Sciences (18th edition, 1990, Chapter 89 "Oral Solid Dosage Forms", pages 1633-1665, which is incorporated herein by reference) using the Schleuniger Apparatus, the tablet/dosage form is put between a pair of flat plates, arranged in parallel, and pressed by means of the flat plates, such that the force is applied substantially perpendicular to the thickness and substantially in line with the diameter of the tablet, thereby reducing the diameter in that direction. This reduced diameter is described in terms of % diameter, based on the diameter of the tablet before conducting the breaking strength test. The breaking strength or tablet hardness is defined as the force at which the tested tablet/dosage form breaks. Tablets/dosage forms that do not break, but which are deformed due to the force applied are considered to be break-resistant at that particular force.

A further test to quantify the strength of tablets/dosage forms is the indentation test using a Texture Analyzer, such as the TA-XT.Plus Texture Analyzer (Texture Technologies Corp., 18 Fairview Road, Scarsdale, NY 10583). In this method, the tablets/dosage forms are placed on top of a stainless steel stand with slightly concaved surface and subsequently penetrated by the descending probe of the Texture Analyzer, such as a TA-8A ⅛ inch diameter stainless steel ball probe. Before starting the measurement, the tablets are aligned directly under the probe, such that the descending probe will penetrate the tablet pivotally, i.e. in the center of the tablet, and such that the force of the descending probe is applied substantially perpendicular to the diameter and substantially in line with the thickness of the tablet. First, the probe of the Texture Analyzer starts to move towards the tablet sample at the pre-test speed. When the probe contacts the tablet surface and the trigger force set is reached, the probe continues its movement with the test speed and penetrates the tablet. For each penetration depth of the probe, which is hereinafter referred to as "distance", the corresponding force is measured, and the data are collected. When the probe has reached the desired maximum penetration depth, it changes direction and moves back at the post-test speed, while further data can be collected. The cracking force is defined to be the force of the first local maximum that is reached in the corresponding force/time diagram and is calculated using for example the Texture Analyzer software "Exponent V6,0,7,0". Without wanting to be bound by any theory, it is believed that at this point, some structural damage to the tablet/dosage form occurs in form of cracking. However, the cracked tablets/dosage forms according to certain embodiments of the invention remain cohesive, as evidenced by the continued resistance to the descending probe. The corresponding distance at the first local maximum is referred to as the "penetration depth to crack" distance.

For purposes of certain embodiments of the invention, the term "breaking strength" refers to the hardness of the tablets/dosage forms that is preferably measured using the Schleuniger apparatus, whereas the term "cracking force" reflects the strength of the tablets/dosage forms that is preferably measured in the indentation test using a Texture Analyzer.

For purposes of the invention the term "active agent" is defined as a pharmaceutically active substance, which includes without limitation opioid agonists, antagonists, and/or opioid analgesics. The term "active agent" encompasses both the free base form of the active agent (aka., "active agent free base" or "active agent free form") and pharmaceutically acceptable salts thereof (i.e., active agent salts). The free base and the pharmaceutically acceptable salts of the active agent may be present in solvent free form, such as in anhydrous form, in solvated form, such as in hydrated form, and as complex, and as mixtures of the foregoing.

For purposes of the invention, the term "opioid agonist" means one or more compounds selected from the group consisting of pure opioid agonists, mixed opioid agonist-antagonists, partial opioid agonists, and mixtures thereof. The term "opioid agonist" encompasses the free base form of the opioid agonist and pharmaceutically acceptable salts thereof (i.e., opioid agonist salts). The free base and the pharmaceutically acceptable salts of the opioid agonist may be present in solvent free form, such as in anhydrous form, in solvated form, such as in hydrated form, and as complex, and as mixtures of the foregoing.

For purposes of the invention, the term "oxycodone" (when used by itself) means oxycodone base, and all pharmaceutically acceptable salts thereof. The oxycodone base and pharmaceutically acceptable salts thereof may be present in solvent free form, such as in anhydrous form, in solvated form, such as in hydrated form, and as complex, and as mixtures of the foregoing. The same meaning applies mutatis mutandis for other specifically mentioned opioid agonists, such as "codeine", "hydrocodone", "hydromorphone", "methadone", "morphine", "oxymorphone", "tramadol", and etc.

The term "opioid analgesic" means one or more compounds having an analgesic effect, which are selected from the group consisting of pure opioid agonists, mixed opioid agonist-antagonists, partial opioid agonists, and mixtures thereof. The term "opioid analgesic" encompasses the free base form of the opioid analgesic and pharmaceutically acceptable salts thereof (i.e., opioid analgesic salts). The free base and the pharmaceutically acceptable salts of the opioid analgesic may be present in solvent free form, such as in anhydrous form, in solvated form, such as in hydrated form, and as complex, and as mixtures of the foregoing.

For purposes of the invention, the term "opioid antagonist" encompasses the free base form of the opioid antagonist and pharmaceutically acceptable salts thereof (i.e., opioid antagonist salts). The free base and the pharmaceutically acceptable salts of the opioid antagonist may be present in solvent free form, such as in anhydrous form, in solvated form, such as in hydrated form, and as complex, and as mixtures of the foregoing.

For purposes of the invention, the term "active agent salt" corresponds to a pharmaceutically acceptable salt of the active agent. The "active agent salt" may be present in solvent free form, such as in anhydrous form, in solvated form, such as in hydrated form, and as complex, and as mixtures of the foregoing. In particular, the term "active agent salt" includes the solvent-free (anhydrous) salt and/or hydrated salts.

For purposes of the invention, the term "opioid agonist salt" and the expression "opioid agonist in salt form" refer to a pharmaceutically acceptable salt of the opioid agonist. The "opioid agonist salt" (and the "opioid agonist in salt form") may be present in solvent free form, such as in anhydrous form, in solvated form, such as in hydrated form, and as complex, and as mixtures of the foregoing. In particular, the term "opioid agonist salt" includes the solvent-free (anhydrous) salt and/or hydrated salts.

For purposes of the invention, the term "opioid antagonist salt" corresponds to a pharmaceutically acceptable salt of the opioid antagonist. The "opioid antagonist salt" may be present in solvent free form, such as in anhydrous form, in solvated form, such as in hydrated form, and as complex, and as mixtures of the foregoing. In particular, the term "opioid antagonist salt" includes the solvent-free (anhydrous) salt and/or hydrated salts.

The term "salt" includes inorganic acid salts, such as hydrochloride, hydrobromide, sulfate, phosphate and the like; and organic acid salts, such as myristate, formate, acetate, trifluoroacetate, maleate, tartrate, bitartrate and the like; sulfonates, such as, methanesulfonate, benzenesulfonate, p-toluenesulfonate and the like; and amino acid salts such as arginate, asparaginate, glutamate and the like.

The terms "codeine phosphate", "hydrocodone bitartrate", "hydromorphone hydrochloride", "methadone hydrochloride", "morphine hydrochloride", "morphine sulfate", "oxycodone hydrochloride", "oxymorphone hydrochloride", and "tramadol hydrochloride" encompass the solvent free form, such as the anhydrous form, solvated forms, such as hydrated forms, and complexes, and mixtures of the foregoing. In particular, the cited terms encompass the solvent-free (anhydrous) salt and/or hydrated salts.

For purposes of the invention, whenever the molecular weight of Mw=351.82 g/mol is added (in parentheses) when oxycodone hydrochloride is referred to, it refers to the oxycodone hydrochloride free of solvents or complexing agents.

The descriptive terms related to the USP water solubility of a substance are defined as follows: 1 g of a very soluble substance dissolves in less than 1 mL of water, 1 g of a freely soluble substance dissolves in 1 to 10 mL of water, 1 g of a soluble substance dissolves in 10 to 30 mL of water, 1 g of a sparingly soluble substance dissolves in 30 to 100 mL of water, 1 g of a slightly soluble substance dissolves in 100 to 1000 mL of water. A substance having a solubility corresponding to the overlapping threshold value between two solubility classes is considered for the purposes of the invention to belong to the higher solubility class. For example, if 1 g of a substance dissolves in 30 mL of water, it is considered as a soluble (and not as a sparingly soluble) substance.

PCT International Publication WO 2005/097801 A1, U.S. Pat. No. 7,129,248 B2, and U.S. Patent Application Publication 2006/0173029 A1, describe a process for preparing oxycodone hydrochloride having a 14-hydroxycodeinone level of less than about 25 ppm, preferably of less than about 15 ppm, less than about 10 ppm, or less than about 5 ppm, more preferably of less than about 2 ppm, less than about 1 ppm, less than about 0.5 ppm or less than about 0.25 ppm. The disclosure of all these afore-mentioned patent documents is hereby incorporated by reference in its entirety.

The term "ppm" as used herein means "parts per million". Regarding 14-hydroxycodeinone, "ppm" means parts per million of 14-hydroxycodeinone in a particular sample product. The 14-hydroxycodeinone level can be determined by any method known in the art, preferably by HPLC analysis using UV detection.

In certain embodiments of the invention, wherein the active agent is oxycodone hydrochloride, oxycodone hydrochloride is used having a 14-hydroxycodeinone level of less than about 25 ppm, less than about 15 ppm, less than about 10 ppm, less than about 5 ppm, less than about 2 ppm, less than about 1 ppm, less than about 0.5 ppm, or less than about 0.25 ppm.

The term "pain" means moderate to severe, acute, and/or chronic pain of malignant and non-malignant origin, in particular severe to most severe, acute and chronic pain of malignant and non-malignant origin, including but not limited to nociceptive pain, neuropathic pain, and visceral pain. Examples include, but are not limited to, severe pain resulting from diseases such as cancer, rheumatism and arthritis. Further examples are post-operative pain, cluster headaches, dental pain, surgical pain, pain resulting from severe burns, pain from third degree burns, back pain, lower back pain, herpes neuralgia, phantom limb pain, central pain, bone injury pain, and pain during labor and delivery.

The term "patient" means a subject, such as a mammal, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

DETAILED DESCRIPTION

Figure 1:
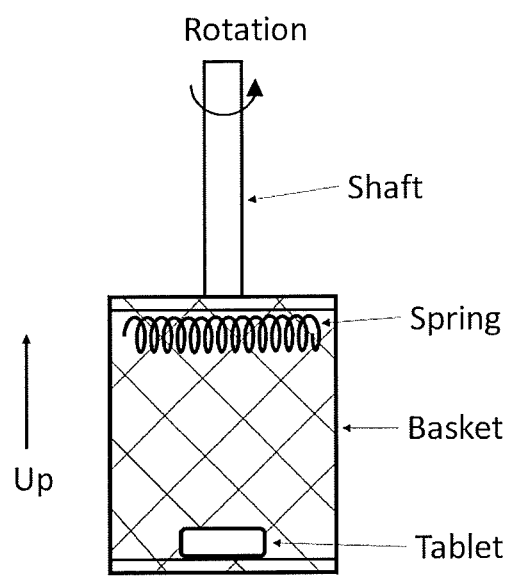
FIG. 1 is a schematic drawing of a USP basket equipped with a retaining spring placed in the upper part of the basket (above the tablet).
Figure 2:
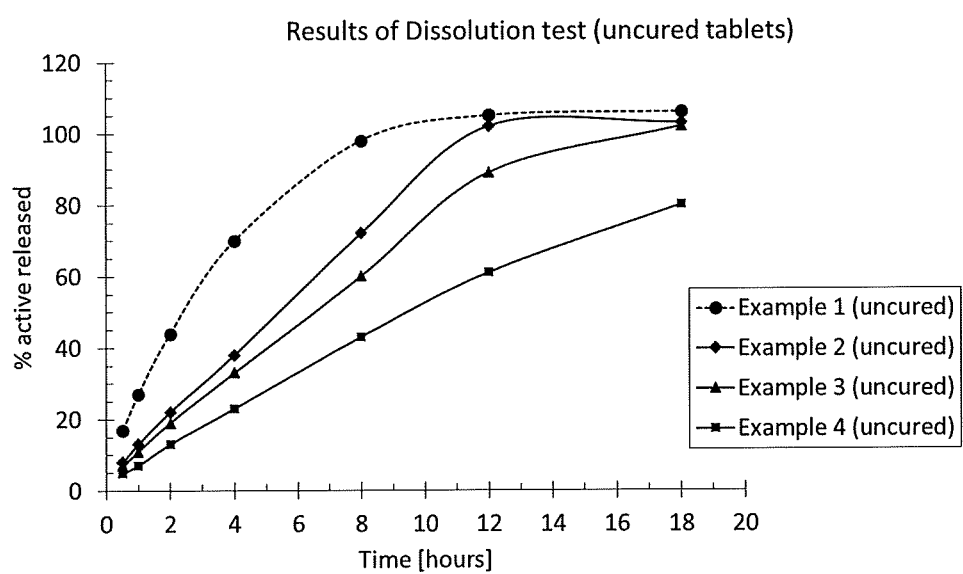
FIG. 2 is a graph depicting the results of the dissolution test of uncured tablets according to Examples 1 to 4.
Figure 3:
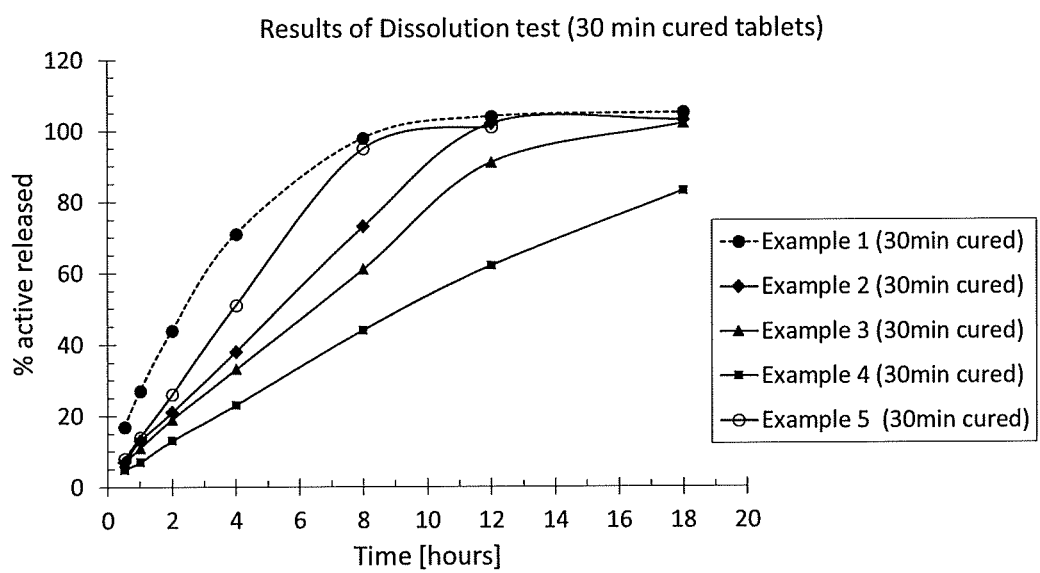
FIG. 3 is a graph depicting the results of the dissolution test of 30 minutes cured tablets according to Examples 1 to 5.
Figure 4:
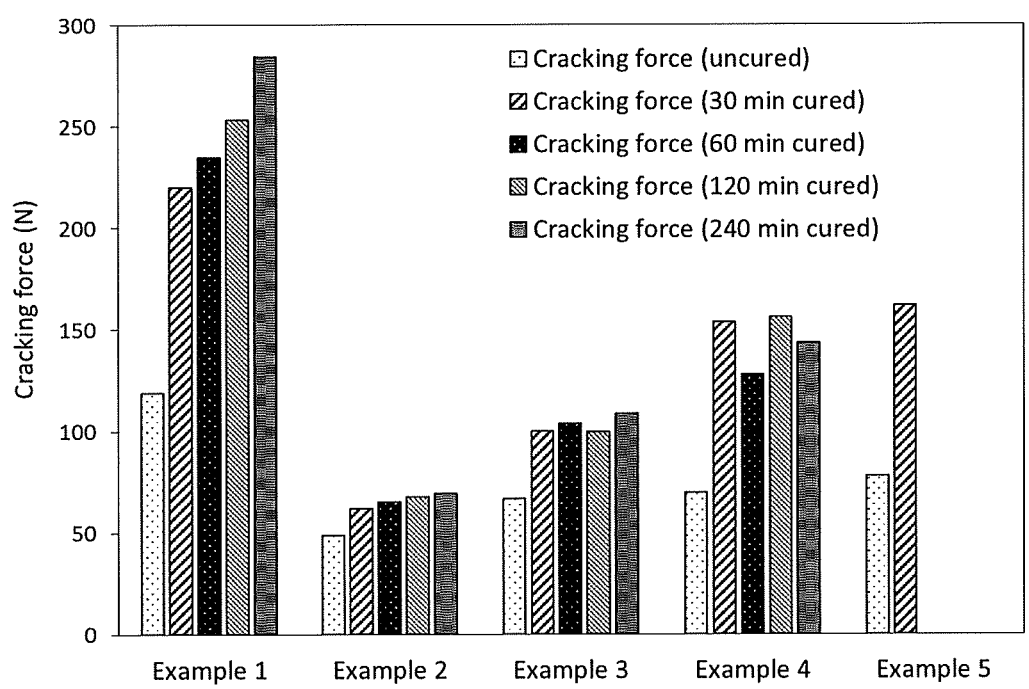
FIG. 4 is a diagram depicting the cracking force measured for uncured and cured tablets of Examples 1 to 5.
Figure 5:
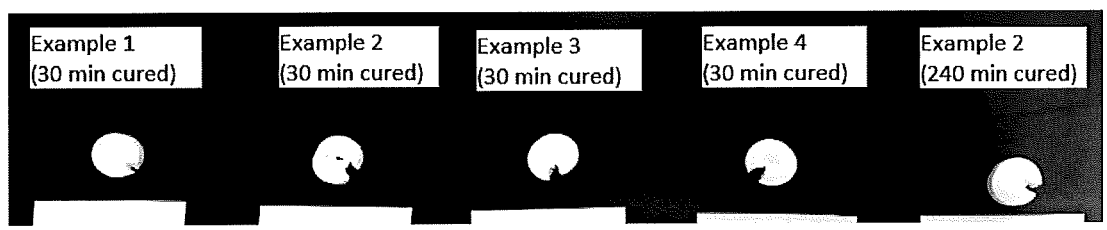
FIG. 5 is a photograph that depicts a top view of cured tablets according to Examples 1 to 4 after the indentation test using a TA-XT.Plus Texture Analyzer.
Figure 6:
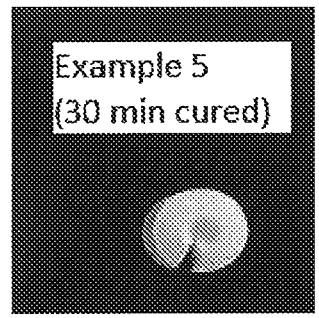
FIG. 6 is a photograph that depicts a top view of a cured tablet according to Example 5 after the indentation test using a TA-XT.Plus Texture Analyzer.

In certain embodiments, the invention is directed to a solid oral extended release pharmaceutical dosage form comprising an extended release matrix formulation, the extended release matrix formulation comprising:

(1) at least one active agent;
(2) at least one anionic surfactant; and
(3) at least about 40% by weight (based on the weight of the extended release matrix formulation) of at least one polyethylene oxide.

In certain embodiments, the molar ratio of the at least one anionic surfactant to the at least one active agent is from about 1:2 to about 10:1. It is understood that the at least one active agent is present in the pharmaceutical dosage form in a pharmaceutically effective amount.

In certain embodiments, the molar ratio of the at least one anionic surfactant to the at least one active agent is from about 8:10 to about 8:1, or from about 8:10 to about 5:1, or from about 2:1 to about 8:1, or from about 2:1 to about 5:1, or from about 3:1 to about 4:1.

Without wishing to be bound by any theory, it is believed that, in certain instances, an observable straightening of the release profile towards zero-order release kinetics in the presence of an anionic surfactant, such as sodium lauryl sulfate, can, inter alia, be attributed to an interaction between the active agent molecule (such as, a cationic/protonated form thereof) and the anionic surfactant. In certain embodiments, wherein for example the anionic surfactant is added to the formulation as a salt having a bivalent cationic counterion, e.g., $Ca^{2+}$, the molar amount to be considered for determining the molar ratio of the at least one anionic surfactant to the at least one active agent is the molar amount of the anionic compound, and not the molar amount of the bivalent cationic counterion. Likewise, in other embodiments, wherein the active agent is included as active agent salt comprising a cationic active agent molecule and an anionic counterion, the molar amount of the cationic active agent molecule is decisive.

In certain embodiments, the extended release matrix formulation comprises at least about 40% by weight (based on the weight of the extended release matrix formulation) of at least one polyethylene oxide having, based on rheological measurements, an approximate molecular weight of from 900,000 to 8,000,000, or from 1,000,000 to 8,000,000, or from 4,000,000 to 8,000,000. In certain embodiments, the at least one polyethylene oxide has, based on rheological measurements, an approximate molecular weight of 1,000,000, 2,000,000, 4,000,000, 5,000,000, 7,000,000, or 8,000,000. In certain such embodiments, the at least one polyethylene oxide has, based on rheological measurements, an approximate molecular weight of 4,000,000, 5,000,000, 7,000,000, or 8,000,000. In certain such embodiments, the at least one polyethylene oxide has, based on rheological measurements, an approximate molecular weight of 4,000,000 or 5,000,000. In certain preferred embodiments, the at least one polyethylene oxide has, based on rheological measurements, an approximate molecular weight of 4,000,000.

For example, the following polyethylene oxide grades are commercially available from Dow Chemical company under the tradename POLYOX® Water-Soluble Resins NF, and can be used in embodiments of the invention:

| PEO grade | Approximate molecular weight[1] |
|---|---|
| POLYOX ® WSR-1105 NF | 900,000 |
| POLYOX ® WSR N-12K NF | 1,000,000 |
| POLYOX ® WSR N-60K NF | 2,000,000 |
| POLYOX ® WSR-301 NF | 4,000,000 |
| POLYOX ® WSR Coagulant NF | 5,000,000 |
| POLYOX ® WSR-303 NF | 7,000,000 |

[1]based on rheological measurements

In certain embodiments, the extended release matrix formulation comprises from about 50% by weight to about 90% by weight of said at least one polyethylene oxide, or from about 60% by weight to about 90% by weight of said at least one polyethylene oxide, or from about 70% by weight to about 85% by weight of said at least one polyethylene oxide, or from about 70% by weight to about 80% by weight of said at least one polyethylene oxide. The indicated weight percentage values are based on the weight of the extended release matrix formulation. In such embodiments, polyethylene oxide having an approximate molecular weight as indicated above can be used.

In certain embodiments, the extended release matrix formulation comprises from about 50% by weight to about 90% by weight, or from about 60% by weight to about 90% by weight, or from about 70% by weight to about 85% by weight, or from about 70% by weight to about 80% by weight of at least one polyethylene oxide having, based on rheological measurements, an approximate molecular weight of from 4,000,000 to 8,000,000. The indicated weight percentage values are based on the weight of the extended release matrix formulation.

In certain embodiments, the at least one anionic surfactant is selected from the group consisting of alkyl carboxylates and fatty acid salts, esters of fatty acids, alkyl ether carboxylates, alkyl sulfonates, alpha-olefin sulfonates, alkyl aryl sulfonates, sulfosuccinates, sulfonated fatty acid esters, ethoxylated alkyl sulfates, alkyl sulfates, fatty alcohol ether sulfates, acyl lactylates, N-acyl sarcosinates, alkyl carbonates, N-acyl glutamates, alkyl phosphates, alkylether phosphates, or mixtures thereof. In certain embodiments, the at least one anionic surfactant is selected from the group consisting of alkyl carboxylates and fatty acid salts, alkyl sulfonates, alpha-olefin sulfonates, alkyl aryl sulfonates, such as alkyl benzene sulfonates, sulfosuccinates, ethoxylated alkyl sulfates, alkyl sulfates, or mixtures thereof.

In certain embodiments, the cationic counterion of the at least one anionic surfactant is selected from sodium, potassium, ammonium ($NH_4^+$), alkanolammonium, or mixtures thereof. In certain such embodiments, the cationic counterion of the at least one anionic surfactant is selected from sodium, potassium, ammonium, ethanolammonium, diethanolammonium, triethanolammonium, or mixtures thereof. In certain such embodiments, the cationic counterion of the at least one anionic surfactant is selected from sodium and potassium, or mixtures thereof. In certain such embodiments, the cationic counterion of the at least one anionic surfactant is sodium.

In certain embodiments, the alkyl carboxylates are ($C_7$-$C_{17}$) alkyl carboxylates (i.e., have a chain length of from 8 to 18 carbon atoms) and the fatty acid salts have a chain length of from 8 to 18 carbon atoms. In certain embodiments, the alkyl carboxylates are ($C_{11}$-$C_{17}$) alkyl carboxylates and the fatty acid salts have a chain length of from 12 to 18 carbon atoms. Examples of this group include potassium laurate, sodium laurate, sodium palmitate, sodium caprylate, sodium stearate, and sodium oleate.

In certain embodiments, the alkyl sulfonates are primary or secondary ($C_{10}$-$C_{18}$) alkyl sulfonates. In certain embodiments, the alkyl sulfonates are primary ($C_{10}$-$C_{18}$) n-alkyl sulfonates. Examples of this group include sodium octane sulfonate, sodium decane sulfonate, and sodium dodecane sulfonate.

In certain embodiments, the alpha-olefin sulfonates are primary ($C_{10}$-$C_{18}$) alpha-olefin sulfonates. In certain such embodiments, the alpha-olefin sulfonates have a linear alkenyl moiety. An example of this group is sodium ($C_{14}$-$C_{16}$) alpha olefin sulfonate.

In certain embodiments, the alkyl aryl sulfonates are ($C_8$-$C_{16}$) alkyl benzene sulfonates. In certain embodiments, the alkyl aryl sulfonates are ($C_{10}$-$C_{16}$) n-alkyl benzene sulfonates. An example of this group is sodium n-dodecylbenzene sulfonate.

In certain embodiments, the sulfosuccinates are di($C_4$-$C_{10}$) alkyl sulfosuccinates. Examples of this group include sodium bis-(2-ethylhexyl) sulfosuccinate or docusate sodium, and diamyl sodium sulfosuccinate.

In certain embodiments, the ethoxylated alkyl sulfates have the formula $R_1$—$O(CH_2CH_2O)_p$—$SO_3M$, wherein $R_1$ is a ($C_8$-$C_{20}$) alkyl, p is an integer from 1 to 8, and M is sodium, potassium, ammonium or an alkanolammonium (e.g., ethanolammonium, diethanolammonium, triethanolammonium). In certain embodiments, the ethoxylated alkyl sulfates have the formula $R_1$—$O(CH_2CH_2O)_p$—$SO_3M$, wherein $R_1$ is a ($C_{10}$-$C_{18}$) alkyl, p is an integer from 2 to 6, and M is sodium, potassium, ammonium or an alkanolammonium. In certain embodiments, the ethoxylated alkyl sulfates have the formula $R_1$—$O(CH_2CH_2O)_p$—$SO_3M$, wherein $R_1$ is a ($C_{12}$-$C_{15}$) alkyl, p is an integer from 2 to 4, and M is sodium or potassium, ammonium or an alkanolammonium. In certain such embodiments, M is sodium or potassium.

In certain embodiments, the alkyl sulfates are primary or secondary ($C_8$-$C_{26}$) alkyl sulfates. In certain embodiments, the alkyl sulfates are primary or secondary ($C_8$-$C_{22}$) alkyl sulfates. In certain embodiments, the alkyl sulfates are primary ($C_8$-$C_{22}$) n-alkyl sulfates. Examples of this group include sodium n-octyl sulfate, sodium n-decyl sulfate, sodium n-dodecyl sulfate, sodium lauryl sulfate, sodium n-tetradecyl sulfate, sodium n-hexadecyl sulfate, and sodium n-octadecyl sulfate.

In certain embodiments, the at least one anionic surfactant is selected from the group consisting of primary or secondary ($C_8$-$C_{18}$) alkyl sulfates. In certain such embodiments, the at least one anionic surfactant is selected from the group consisting of primary or secondary sodium ($C_8$-$C_{18}$) alkyl sulfates, potassium ($C_8$-$C_{18}$) alkyl sulfates, ammonium ($C_8$-$C_{18}$) alkyl sulfates, alkanolammonium ($C_8$-$C_{18}$) alkyl sulfates, or mixtures thereof. In certain such embodiments, the at least one anionic surfactant is selected from the group consisting of primary or secondary sodium ($C_8$-$C_{18}$) alkyl sulfates, potassium ($C_8$-$C_{18}$) alkyl sulfates, ammonium ($C_8$-$C_{18}$) alkyl sulfates, ethanolammonium ($C_8$-$C_{18}$) alkyl sulfates, diethanolammonium ($C_8$-$C_{18}$) alkyl sulfates, triethanolammonium ($C_8$-$C_{18}$) alkyl sulfates, or mixtures thereof. In certain such embodiments, the at least one anionic surfactant is selected from the group consisting of primary or secondary sodium ($C_8$-$C_{18}$) alkyl sulfates and potassium ($C_8$-$C_{18}$) alkyl sulfates. In certain embodiments, the at least one anionic surfactant is selected from the group consisting of primary or secondary sodium ($C_8$-$C_{18}$) alkyl sulfates.

In certain embodiments, the at least one anionic surfactant is selected from primary ($C_8$-$C_{18}$) n-alkyl sulfates. In certain such embodiments, the at least one anionic surfactant is selected from the group consisting of primary sodium ($C_8$-$C_{18}$) n-alkyl sulfates, potassium ($C_8$-$C_{18}$) n-alkyl sulfates, ammonium ($C_8$-$C_{18}$) n-alkyl sulfates, alkanolammonium ($C_8$-$C_{18}$) n-alkyl sulfates, or mixtures thereof. In certain such embodiments, the at least one anionic surfactant is selected from the group consisting of primary sodium ($C_8$-$C_{18}$) n-alkyl sulfates, potassium ($C_8$-$C_{18}$) n-alkyl sulfates, ammonium ($C_8$-$C_{18}$) n-alkyl sulfates, ethanolammonium ($C_8$-$C_{18}$) n-alkyl sulfates, diethanolammonium ($C_8$-$C_{18}$) n-alkyl sulfates, triethanolammonium ($C_8$-$C_{18}$) n-alkyl sulfates, or mixtures thereof. In certain such embodiments, the at least one anionic surfactant is selected from the group consisting of primary sodium ($C_8$-$C_{18}$) n-alkyl sulfates and primary potassium ($C_8$-$C_{18}$) n-alkyl sulfates. In certain embodiments, the at least one anionic surfactant is selected from the group consisting of primary sodium ($C_8$-$C_{18}$) n-alkyl sulfates.

In certain embodiments, the at least one anionic surfactant is selected from lauryl sulfates. In certain such embodiments, the at least one anionic surfactant is selected from sodium lauryl sulfate, potassium lauryl sulfate, ammonium lauryl sulfate, alkanolammonium lauryl sulfate, or mixtures thereof. In certain such embodiments, the at least one anionic surfactant is selected from sodium lauryl sulfate, potassium lauryl sulfate, ammonium lauryl sulfate, ethanolammonium lauryl sulfate, diethanolammonium lauryl sulfate, triethanolammonium lauryl sulfate, or mixtures thereof. In certain such embodiments, the at least one anionic surfactant is selected from sodium lauryl sulfate and potassium lauryl sulfate. In certain such embodiments, the at least one anionic surfactant is sodium lauryl sulfate.

In certain embodiments, the extended release matrix formulation comprises from about 5% by weight to about 25% by weight, or from about 10% by weight to about 25% by weight, or from about 15% by weight to about 25% by weight of said at least one anionic surfactant. The indicated weight percentage values are based on the weight of the extended release matrix formulation.

In certain embodiments, the at least one active agent included in the extended release matrix formulation is at least one active agent salt comprising a cationic active agent molecule and an anionic counterion.

In certain embodiments, the at least one active agent (or active agent salt) has a USP water solubility selected from sparingly soluble, soluble, freely soluble, very soluble, or mixtures thereof. In certain such embodiments, the at least one active agent salt has a USP water solubility selected from soluble, freely soluble, very soluble, or mixtures thereof.

In certain embodiments, the at least one active agent containing an amine group in its structure. In certain embodiments, the amine group is a tertiary amine group. In certain such embodiments, the amine group is a tertiary amine group comprising a ring nitrogen within a five-membered or six-membered ring.

In certain embodiments, wherein the at least one active agent is at least one active agent salt comprising a cationic active agent molecule and an anionic counterion, the cationic active agent molecule of the at least one active agent salt contains an ammonium group in its structure. In certain such embodiments, the ammonium group is a tertiary ammonium group. In certain embodiments, the ammonium group is a tertiary ammonium group comprising a ring nitrogen within a five-membered or six-membered ring.

In certain embodiments, the at least one active agent comprises an opioid agonist. In certain embodiments, the at least one active agent can, for example, comprise an opioid antagonist. Suitable opioid antagonists include naloxone (e.g., naloxone hydrochloride), naltrexone, methylnaltrexone, and nalmephene. In certain embodiments, the opioid antagonist is in salt form. In certain embodiments, the pharmaceutical dosage form comprises an opioid agonist and an opioid antagonist, wherein both are in salt form.

In certain embodiments, the at least one active agent is an opioid agonist. In certain embodiments, the opioid agonist is in salt form. In other embodiments, the opioid agonist is in free form.

In certain embodiments, the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, or mixtures thereof. In certain such embodiments, the opioid agonist is selected from the group consisting of codeine, hydrocodone, hydromorphone, methadone, morphine, oxycodone, oxymorphone, and tramadol. In certain embodiments, the opioid agonist is oxycodone. In certain embodiments, the above-listed opioid agonists are in salt form. In the case of such opioid agonist salts, the active agent molecule is cationic, preferably due to protonation of a basic group, e.g., an amine group within the chemical structure. In certain embodiments, the opioid agonist salts comprise an anionic counterion selected from chloride, bitartrate, tartrate, sulfate, phosphate, and terephthalate. In other embodiments, the above-listed opioid agonists are in free form.

In certain embodiments, the at least one active agent is selected from the group consisting of codeine phosphate, hydrocodone bitartrate, hydromorphone hydrochloride, methadone hydrochloride, morphine hydrochloride, morphine sulfate, oxycodone hydrochloride, oxymorphone hydrochloride, and tramadol hydrochloride. In certain embodiments, the at least one active agent comprises one or more of the compounds of this group.

In certain embodiments, the at least one active agent is selected from the group consisting of hydrocodone bitartrate, morphine hydrochloride, morphine sulfate, and oxycodone hydrochloride. In certain embodiments, the at least one active agent comprises one or more of the compounds of this group.

In certain preferred embodiments, the at least one active agent is or comprises oxycodone hydrochloride. In certain such embodiments, the dosage form comprises a total amount of oxycodone hydrochloride which is equimolar to from about 5 mg to about 160 mg of oxycodone hydrochloride (Mw=351.82 g/mol). In certain such embodiments, the dosage form comprises a total amount of oxycodone hydrochloride which is equimolar to from about 5 mg to about 120 mg of oxycodone hydrochloride (Mw=351.82 g/mol). In certain such embodiments, the dosage form comprises a total amount of oxycodone hydrochloride which is equimolar to from about 10 mg to about 80 mg of oxycodone hydrochloride (Mw=351.82 g/mol).

In certain embodiments, the at least one active agent is selected from the group of antihistamines (e.g., dimenhydrinate, diphenhydramine, chlorpheniramine and dexchlorpheniramine maleate); non-steroidal anti-inflammatory agents (e.g., naproxen, diclofenac, indomethacin, ibuprofen, sulindac, Cox-2 inhibitors) and acetaminophen; anti-emetics (e.g., metoclopramide, meth-5-ylnaltrexone); anti-epileptics (e.g., phenyloin, meprobmate and nitrazepam); vasodilators (e.g., nifedipine, papaverine, diltiazem and nicardipine); anti-tussive agents and expectorants (e.g. codeine phosphate); anti-asthmatics (e.g., theophylline); antacids; antispasmodics (e.g. atropine, scopolamine); antidiabetics (e.g., insulin); diuretics (e.g., ethacrynic acid, bendrofluthiazide); anti-hypotensives (e.g., propranolol, clonidine); antihypertensives (e.g., clonidine, methyldopa); bronchodilatiors (e.g., albuterol); steroids (e.g., hydrocortisone, triamcinolone, prednisone); antibiotics (e.g., tetracycline); antihemorrhoidals; hypnotics; psychotropics; antidiarrheals; mucolytics; sedatives; decongestants (e.g. pseudoephedrine); laxatives; vitamins; stimulants, including CNS-stimulants (e.g., methylphenidate, amphetamine, dextroamphetamine, and mazindol) and appetite suppressants (such as, phenylpropanolamine), and cannabinoids. It is understood that the above-described active agents can be used in either free base or salt form, either of which can be in anhydrous form or in solvated form. In certain embodiments, the active agent employed in the pharmaceutical dosage form is in salt form.

In separate embodiments, one of the aforementioned active agents is present as the sole active agent in the pharmaceutical dosage form. In other embodiments, one of the above-described active agents is present along with one or more other active agents (such as, opioid agonists and opioid antagonists) in the pharmaceutical dosage form.

In certain embodiments, the extended release matrix formulation comprises from about 2% by weight to about 35% by weight, or from about 2% by weight to about 25% by weight, or from about 2% by weight to about 20% by weight of said at least one active agent (or active agent salt). The indicated weight percentage values are based on the weight of the extended release matrix formulation.

In certain embodiments, the dosage form and/or the extended release matrix formulation comprise the above described at least one active agent (or active agent salt) as the sole active agent.

In certain embodiments, the dosage form and/or the extended release matrix formulation comprise one or more opioid agonists (either free bases or salts) (as described above) as the only active agent(s). In certain other embodiments, the dosage form and/or the extended release matrix formulation comprise a combination of an opioid agonist (salt) with an opioid antagonist (salt) as the only active agents.

In certain embodiments, the dosage form and/or the extended release matrix formulation comprise one or more opioid antagonists (either as free bases or salts) as the sole active agent(s). In certain other embodiments, the dosage form and/or the extended release matrix formulation comprise a combination of an opioid antagonist (in the salt form) with an opioid agonist (in the salt form) as the active agents.

In certain embodiments, the extended release matrix formulation further comprises a lubricant. In certain such embodiments, the extended release matrix formulation comprises from about 0.5% by weight to about 5% by weight of the lubricant, from about 0.5% by weight to about 2% by weight of the lubricant, or from about 0.5% by weight to about 1.5% by weight of the lubricant. The indicated weight percentage values are based on the weight of the extended release matrix formulation. In certain embodiments, the lubricant is magnesium stearate. Other suitable lubricants include, but are not limited to calcium stearate, glyceryl monostearate, glyceryl behenate, glyceryl palmitostearate, magnesium lauryl sulfate, sodium lauryl sulfate, sodium stearyl fumarate, zinc stearate, stearic acid, and mixtures thereof. If a lubricant is used, the lubricant is different from the compound(s) used as anionic surfactant.

In certain embodiments, the at least one active agent (either free base or salt), the at least one anionic surfactant, the at least one polyethylene oxide, and an optional lubricant together make up from about 95% by weight to about 100% by weight of the extended release matrix formulation. In certain such embodiments, the at least one active agent (either free base or salt), the at least one anionic surfactant, the at least one polyethylene oxide, and an optional lubricant together make up from about 97% by weight to about 100% by weight of the extended release matrix formulation.

In certain embodiments, the extended release matrix formulation is cured by subjecting the extended release matrix formulation to a temperature which is at least the softening temperature of said polyethylene oxide for a time period of at least about 1 minute. In certain embodiments, the curing step is conducted at atmospheric pressure.

In certain embodiments, the extended release matrix formulation is cured by subjecting the extended release matrix formulation to a temperature of from about 60° C. to about 90° C. for a time period of from about 1 minute to about 24 hours. In certain embodiments, the curing step is conducted at atmospheric pressure.

In certain embodiments, the extended release matrix formulation is cured by subjecting the extended release matrix formulation to a temperature of from about 62° C. to about 85° C. for a time period of from about 5 minutes to about 5 hours. In certain embodiments, the curing step is conducted at atmospheric pressure.

In certain embodiments, the extended release matrix formulation is cured by subjecting the extended release matrix formulation to a temperature of from about 65° C. to about 85° C. for a time period of from about 15 minutes to about 2 hours. In certain embodiments, the curing step is conducted at atmospheric pressure.

In certain embodiments, the extended release matrix formulation comprised in the pharmaceutical dosage form has an overall weight of from about 80 mg to about 320 mg, or from about 100 mg to about 300 mg, or from about 120 mg to about 280 mg.

In certain embodiments, the extended release matrix formulation is in the form of a tablet. In certain such embodiments, the extended release matrix formulation is in the form of a tablet and overcoated with a (protective and/or cosmetic) film coating. Suitable film coating materials are known to the skilled person.

In certain embodiments, the extended release matrix formulation when subjected to an indentation test has a cracking force of at least about 100 N, or of at least about 120 N, or of at least about 140 N.

The parameter "cracking force" is determined in an indentation test as described above, using a Texture Analyzer such as the TA-XT.Plus Texture Analyzer (Texture Technologies Corp., 18 Fairview Road, Scarsdale, NY 10583). The cracking force can be determined using an uncoated or a coated extended release matrix formulation. Preferably, the cracking force is determined on the uncoated extended release matrix formulation. Without wanting to be bound by any theory, it is believed that a coating, such as the film coating mentioned above, does not significantly contribute to the observed cracking force. Therefore, the cracking force determined for a specific coated extended release matrix formulation is not expected to vary substantially from the values determined for the corresponding uncoated extended release matrix formulation.

In certain embodiments, the extended release matrix formulation when subjected to a tablet hardness test has a breaking strength of at least about 140 N.

Preferably, the tablet hardness test to determine the breaking strength of extended release matrix formulations is performed in a Schleuniger Apparatus as described above. For example, the breaking strength is determined using a Schleuniger 8M Apparatus and applying a force of a maximum of about 400 N.

In certain embodiments, the extended release matrix formulation does not break, when subjected to a maximum force of about 400 N in a tablet hardness test.

Without wishing to be bound by any theory, it is believed that higher contents of polyethylene oxide in the extended release matrix formulation, in particular higher contents of polyethylene oxide having an approximate molecular weight of at least 1,000,000, increase the cracking force and/or the breaking strength of the extended release matrix formulation.

In Vitro Dissolution

In certain embodiments, the solid oral extended release pharmaceutical dosage form as described herein provides a substantially zero order release of the at least one active agent (or active agent salt) contained therein over a time period of at least 4 hours, e.g. from 4 hours to 8 hours).

In certain embodiments, the solid oral extended release pharmaceutical dosage form as described herein, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released at x hours, wherein x is an integer selected from a number between 2 and 12; and an amount of the at least one active agent released at y hours, wherein y is an integer selected from a number between 6 and 24, and y≥x+4;

which complies at least for one combination of x and y with equations (I) and (II):

$$\text{the amount released at } y \text{ hours} \leq \left(\frac{y}{x} \times \text{amount released at } x \text{ hours}\right) \times 1.25 \quad \text{(I)}$$

-continued $$\text{the amount released at } y \text{ hours} \geq \left(\frac{y}{x} \times \text{amount released at } x \text{ hours}\right) \times 0.75. \quad (II)$$

In certain embodiments, the solid oral extended release pharmaceutical dosage form as described herein, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released at x hours, wherein x is an integer selected from a number between 2 and 12; and an amount of the at least one active agent released at y hours, wherein y is an integer selected from a number between 6 and 24, and y≥x+4;

which complies at least for one combination of x and y with equations (I') and (II'):

$$\text{the amount released at } y \text{ hours} \leq \left(\frac{y}{x} \times \text{amount released at } x \text{ hours}\right) \times 1.2 \quad (I')$$

$$\text{the amount released at } y \text{ hours} \geq \left(\frac{y}{x} \times \text{amount released at } x \text{ hours}\right) \times 0.8. \quad (II')$$

In certain embodiments, the solid oral extended release pharmaceutical dosage form as described herein, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released at x hours, wherein x is an integer selected from a number between 2 and 12; and an amount of the at least one active agent released at y hours, wherein y is an integer selected from a number between 6 and 24, and y≥x+4;

which complies at least for one combination of x and y with equations (I") and (II"):

$$\text{the amount released at } y \text{ hours} \leq \left(\frac{y}{x} \times \text{amount released at } x \text{ hours}\right) \times 1.1 \quad (I'')$$

$$\text{the amount released at } y \text{ hours} \geq \left(\frac{y}{x} \times \text{amount released at } x \text{ hours}\right) \times 0.9. \quad (II'')$$

In certain such embodiments, x is an integer selected from a number between 2 and 8, and y is an integer selected from a number between 8 and 24, and y≥x+4.

In certain embodiments, the dissolution rate complies with the cited equations (i.e., equations (I) and (II), or equations (I') and (II'), or equations (I") and (II")), at least for the combination of x and y, wherein x is 4 and y is 8.

In certain embodiments, the dissolution rate complies with the cited equations, at least for the combination of x and y, wherein x is 2 and y is 8.

In certain embodiments, the dissolution rate complies with the cited equations, at least for the combination of x and y, wherein x is 8 and y is 12.

In certain embodiments, the dissolution rate complies with the cited equations, at least for the combination of x and y, wherein x is 4 and y is 12.

In certain embodiments, the dissolution rate complies with the cited equations, at least for the combination of x and y, wherein x is 2 and y is 12.

In certain embodiments, the dissolution rate complies with the cited equations, at least for the combination of x and y, wherein x is 8 and y is 18.

In certain embodiments, the dissolution rate complies with the cited equations, at least for the combination of x and y, wherein x is 4 and y is 18.

In certain embodiments, the dissolution rate complies with the cited equations, at least for the combination of x and y, wherein x is 8 and y is 24.

In certain such embodiments, the dissolution rate complies with the cited equations, for two or more of the above individually cited combinations of x and y. For example, in certain embodiments, the dissolution rate complies with the cited equations, at least for the combinations wherein (1) x is 4 and y is 8 and (2) x is 2 and y is 8. In certain embodiments, the dissolution rate complies with the cited equations, at least for the combinations wherein (1) x is 4 and y is 8 and (2) x is 8 and y is 12. In certain embodiments, the dissolution rate complies with the cited equations, at least for the combinations wherein (1) x is 4 and y is 8; (2) x is 2 and y is 8, and (3) x is 8 and y is 12.

In certain embodiments, the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released (such as the at least one opioid agonist released), which meets at least one of the following criteria:

(i) at 2 hours, the amount released is from about 5% to about 30%;
(ii) at 4 hours, the amount released is from about 10% to about 60%;
(iii) at 8 hours, the amount released is from about 25% to about 100%;
(iv) at 12 hours, the amount released is from about 40% to about 100%;
(v) at 18 hours, the amount released is from about 60% to about 100%;
(vi) at 24 hours, the amount released is from about 80% to about 100%.

In one embodiment, the dosage form of the invention provides a dissolution profile, in which two or more of criteria (i) to (vi) are met. In another embodiment, the dosage form of the invention provides a dissolution profile, in which three or more of criteria (i) to (vi) are met. In still another embodiment, the dosage form of the invention provides a dissolution profile, in which four or more of criteria (i) to (vi) are met. In yet another embodiment, the dosage form of the invention provides a dissolution profile, in which at least five of criteria (i) to (vi) are met. In a particular embodiment, the dosage form of the invention provides a dissolution profile, in which all criteria (i) to (vi) are met.

In certain embodiments, the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released (such as the at least one opioid agonist released), which meets at least one of the following criteria:

(i) at 2 hours, the amount released is from about 5% to about 20%;
(ii) at 4 hours, the amount released is from about 10% to about 30%;
(iii) at 8 hours, the amount released is from about 25% to about 60%;
(iv) at 12 hours, the amount released is from about 40% to about 80%;
(v) at 18 hours, the amount released is from about 60% to about 95%;
(vi) at 24 hours, the amount released is from about 80% to about 100%.

In certain embodiments, the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released (such as the at least one opioid agonist released), which meets at least one of the following criteria:
(i) at 2 hours, the amount released is from about 5% to about 20%;
(ii) at 4 hours, the amount released is from about 10% to about 30%;
(iii) at 8 hours, the amount released is from about 25% to about 55%;
(iv) at 12 hours, the amount released is from about 45% to about 75%;
(v) at 18 hours, the amount released is from about 70% to about 90%;
(vi) at 24 hours, the amount released is from about 85% to about 100%.

In certain embodiments, the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released (such as the at least one opioid agonist released), which meets at least one of the following criteria:
(i) at 2 hours, the amount released is from about 5% to about 15%;
(ii) at 4 hours, the amount released is from about 15% to about 30%;
(iii) at 8 hours, the amount released is from about 30% to about 45%;
(iv) at 12 hours, the amount released is from about 45% to about 70%;
(v) at 18 hours, the amount released is from about 70% to about 90%;
(vi) at 24 hours, the amount released is from about 90% to about 100%.

In certain embodiments, the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released (such as the at least one opioid agonist released), which meets at least one of the following criteria:
(i) at 2 hours, the amount released is from about 10% to about 30%;
(ii) at 4 hours, the amount released is from about 25% to about 60%;
(iii) at 8 hours, the amount released is from about 55% to about 100%;
(iv) at 12 hours, the amount released is from about 80% to about 100%.

Manufacture of Dosage Forms

In certain embodiments, the solid oral extended release pharmaceutical dosage form as described herein is manufactured by a process comprising the steps of
(a) combining at least
   (1) at least one active agent;
   (2) at least one anionic surfactant; and
   (3) at least about 40% by weight (based on the weight of the extended release matrix formulation) of at least one polyethylene oxide;
   to form a composition;
(b) shaping the composition to form an extended release matrix formulation; and
(c) optionally curing said extended release matrix formulation comprising at least a curing step of subjecting the extended release matrix formulation to a temperature which is at least the softening temperature of said polyethylene oxide for a time period of at least about 1 minute.

In certain such embodiments, the molar ratio of the at least one anionic surfactant to the at least one active agent is from about 1:2 to about 10:1. In certain such embodiments, the molar ratio of the at least one anionic surfactant to the at least one active agent is from about 1:2 to about 10:1, and the at least one active agent is at least one active agent salt comprising a cationic active agent molecule and an anionic counterion.

The process of manufacture, and in particular the shaping step b) and the curing step c) including curing temperatures, curing times with starting points and end points of the curing, and devices used for the curing step, can be conducted in analogy to the teaching of PCT publication WO 2008/023261, in particular paragraphs [0046], [00126] to [00146], [00159] to [00161] thereof, the contents of which are hereby incorporated by reference.

In certain embodiments, the composition is shaped in step b) to form an extended release matrix formulation in the form of a tablet. For shaping the extended release matrix formulation in the form of a tablet, a direct compression process can be used. Direct compression is an efficient and simple process for shaping tablets by avoiding process steps like wet granulation. However, any other process for manufacturing tablets as known in the art may also be used, such as wet granulation and subsequent compression of the granules to form tablets. The shaping step b) may also be carried out by an extrusion process, or by a molding process (due to the elevated temperature applied during curing or molding, a subsequent curing step c) may not be necessary).

In certain embodiments, the curing of step c) is conducted at atmospheric pressure.

In certain embodiments, the curing of step c) is conducted by subjecting the extended release matrix formulation to a temperature of from about 60° C. to about 90° C. for a time period of from about 1 minute to about 24 hours.

In certain embodiments, the curing of step c) is conducted by subjecting the extended release matrix formulation to a temperature of from about 62° C. to about 85° C. for a time period of from about 5 minutes to about 5 hours.

In certain embodiments, the curing of step c) is conducted by subjecting the extended release matrix formulation to a temperature of from about 65° C. to about 85° C. for a time period of from about 15 minutes to about 2 hours.

In certain embodiments, the curing of step c) is conducted such that at least about 20%, or at least about 40%, or at least about 75%, or about 100% of the polyethylene oxide melts.

In certain embodiments, the process as described above comprises a further step d) of coating the optionally cured extended release matrix formulation. In certain such embodiments, the coating is a film coating (e.g., a cosmetic film coating such as an Opadry® coating).

In certain embodiments, an initial film coating or a fraction of a film coating is applied prior to performing curing step c). This film coating provides an "overcoat" for the extended release matrix formulations or tablets to function as an anti-tacking agent, i.e. in order to avoid that the extended release matrix formulations or tablets stick together. In certain such embodiments the film coating which is applied prior to the curing step is an Opadry® film coating. After the curing step c), a further film coating step can be performed.

The invention is also directed to a solid oral extended release pharmaceutical dosage form obtained by a process as described herein.

Methods, Uses, and Products for Use

In certain embodiments, the invention is directed to a method of treating or preventing pain comprising administering to a patient identified in need thereof a therapeutically effective amount of a solid oral extended release pharmaceutical dosage form as described herein. In certain embodiments, the at least one active agent comprises an opioid agonist to provide analgesic effect.

In certain embodiments, the invention is directed to a solid oral extended release pharmaceutical dosage form as described herein, for use in a method of treating or preventing pain. In such embodiments, the at least one active agent comprises an opioid agonist to provide analgesic effect.

In certain embodiments, the invention is directed to the use of an extended release matrix formulation comprising:
(1) at least one active agent;
(2) at least one anionic surfactant; and
(3) at least about 40% by weight (based on the weight of the extended release matrix formulation) of at least one polyethylene oxide;
in a solid oral extended release pharmaceutical dosage form, for achieving a substantially zero order release of the at least one active agent from said dosage form, for example over a time period of at least 4 hours, e.g., from 4 hours to 8 hours of dissolution. In certain such embodiments, the molar ratio of the at least one anionic surfactant to the at least one active agent is from about 1:2 to about 10:1. In certain embodiments, the at least one active agent is at least one active agent salt comprising a cationic active agent molecule and an anionic counterion.

In certain embodiments, the invention is directed to the use of an extended release matrix formulation comprising:
(1) at least one active agent;
(2) at least one anionic surfactant; and
(3) at least about 40% by weight (based on the weight of the extended release matrix formulation) of at least one polyethylene oxide;
in a solid oral extended release pharmaceutical dosage form, for achieving an in-vitro dissolution rate of the dosage form with
an amount of the at least one active agent released at x hours, wherein x is an integer selected from a number between 2 and 12; and
an amount of the at least one active agent released at y hours, wherein y is an integer selected from a number between 6 and 24, and y≥x+4;
which complies at least for one combination of x and y with equations (I) and (II):

$$\text{the amount released at } y \text{ hours} \leq \left(\frac{y}{x} \times \text{amount released at } x \text{ hours}\right) \times 1.25 \quad (I)$$

$$\text{the amount released at } y \text{ hours} \geq \left(\frac{y}{x} \times \text{amount released at } x \text{ hours}\right) \times 0.75, \quad (II)$$

when the dosage form is subjected to an in-vitro dissolution test in a USP Apparatus 1 (basket) at 100 rpm in 900 ml simulated gastric fluid without enzymes (SGF) at 37.0±0.5° C. In certain embodiments, the molar ratio of the at least one anionic surfactant to the at least one active agent is from about 1:2 to about 10:1. In certain embodiments, the at least one active agent is at least one active agent salt comprising a cationic active agent molecule and an anionic counterion.

In certain embodiments, the invention is directed to a method of achieving a substantially zero order release of at least one active agent from a solid oral extended release pharmaceutical dosage form (for example, over a time period of at least 4 hours, e.g., from 4 hours to 8 hours of dissolution), comprising providing said dosage form with an extended release matrix formulation comprising:
(1) said at least one active agent;
(2) at least one anionic surfactant; and
(3) at least about 40% by weight (based on the weight of the extended release matrix formulation) of at least one polyethylene oxide.
In certain embodiments, the molar ratio of the at least one anionic surfactant to the at least one active agent is from about 1:2 to about 10:1. In certain embodiments, the at least one active agent is at least one active agent salt comprising a cationic active agent molecule and an anionic counterion.

In certain embodiments, the invention is directed to a method of achieving an in vitro dissolution rate of at least one active agent from a solid oral extended release pharmaceutical dosage form with
an amount of the at least one active agent released at x hours, wherein x is an integer selected from a number between 2 and 12; and
an amount of the at least one active agent released at y hours, wherein y is an integer selected from a number between 6 and 24, and y≥x+4;
wherein the dissolution rate complies at least for one combination of x and y with equations (I) and (II):

$$\text{amount released at } y \text{ hours} \leq \left(\frac{y}{x} \times \text{amount released at } x \text{ hours}\right) \times 1.25 \quad (I)$$

$$\text{amount released at } y \text{ hours} \geq \left(\frac{y}{x} \times \text{amount released at } x \text{ hours}\right) \times 0.75, \quad (II)$$

when the dosage form is subjected to an in-vitro dissolution test in a USP Apparatus 1 (basket) at 100 rpm in 900 ml simulated gastric fluid without enzymes (SGF) at 37.0±0.5° C., comprising providing said dosage form with an extended release matrix formulation comprising:
(1) said at least one active agent;
(2) at least one anionic surfactant; and
(3) at least about 40% by weight (based on the weight of the extended release matrix formulation) of at least one polyethylene oxide.

In certain embodiments, the molar ratio of the at least one anionic surfactant to the at least one active agent is from about 1:2 to about 10:1. In certain embodiments, the at least one active agent is at least one active agent salt comprising a cationic active agent molecule and an anionic counterion.

In certain uses and methods as described above, the extended release matrix formulation and the in vitro dissolution rate may have the features as described herein above in the context of describing the solid oral extended release pharmaceutical dosage form.

EXAMPLES

The invention is more fully described with reference to the accompanying examples. It should be understood, however, that the following description is illustrative only and should not be taken in any way as a restriction of the invention.

Materials and Test Methods

For the manufacture of tablets according to Examples 1-5 below, the following materials were used:

| Material | Manufacturer/supplier | Lot Number |
|---|---|---|
| Oxycodone hydrochloride | Rhodes Technologies | 29-12 XYK |
| Polyethylene Oxide (POLYOX ® WSR-301 NF) | Dow Chemical | D682F6HPB3 |
| Polyethylene Oxide (POLYOX ® WSR N-12K NF) | Dow Chemical | 1D2455S5L2 |
| Sodium lauryl sulfate (SLS) | Fisher Scientific | 166057 |
| Magnesium Stearate | Peter Greven | C302873 |

For the tablets according to Examples 1-5 below, in-vitro dissolution rate, thickness, hardness (breaking strength) and cracking force were measured as described in the following.

In-vitro dissolution testing of the tablets according to Examples 1-5 below was performed as follows: Tablets (uncured, or cured for a time period as indicated) were tested in vitro using a USP Apparatus 1 (basket) at 100 rpm in 900 ml simulated gastric fluid without enzymes (SGF) at 37.0±0.5° C. To reduce the propensity of the tablets, once hydrated in the dissolution medium, to stick to the solid underside of the top of the basket or the base of the shaft, a retaining spring (passivized stainless steel 316 spring, 1.5-cm outside diameter and 2-cm length) was placed in the upper part of the basket (above the tablet). Sampling time points included 0.5, 1.0, 2.0, 4.0, 8.0, 12.0 and 18.0 hours (or as indicated). The samples were analyzed by reversed-phase high performance liquid chromatography (HPLC) on Waters XBridge phenyl, 4.6×75 mm, 3.5 µm column maintained at 60° C. using a gradient method with mobile phase consisting of acetonitrile and potassium phosphate monobasic and ammonium hexafluorophosphate buffer with UV detection at 285 nm and 212 nm.

The thickness of the tablets according to Examples 1-5 below was measured on uncured tablets and using a digital caliper.

The breaking strength of the tablets according to Examples 1-5 below was measured as follows: Tablets (uncured, or cured for 30 minutes) were subjected to a breaking strength test by applying a force of a maximum of about 400 Newton using a Schleuniger 8M Apparatus to evaluate tablet resistance to breaking.

The cracking force of the tablets according to Examples 1-5 below was measured as follows: Tablets (uncured, or cured for a time period as indicated) were subjected to an indentation test with a Texture Analyzer to quantify the tablet strength. The indentation tests were performed with a TA-XT.Plus Texture Analyzer (Texture Technologies Corp., 18 Fairview Road, Scarsdale, NY 10583) equipped with a TA-8A ⅛ inch diameter stainless steel ball probe. The probe height was calibrated to 6 mm above a stainless stand with slightly concaved surface. The tablets were placed on top of the stainless stand and aligned directly under the probe. Each type of tablet was tested three times (n=3). The reported values correspond to the average of 3 measurements. Testing performed on the same type of tablet produced similar results unless the tablet and the probe were misaligned. In such an event, the data would be rejected upon confirmation by visual examination of the tested tablet. The indentation tests were run with the following parameters: pre-test speed: 0.5 mm/s, test speed: 0.5 mm/s, automatic trigger force: 10 grams, post-test speed: 1.0 mm/s, test distance: 3.0 mm.

The results of the measurements are reported in the respective Examples below.

Example 1

In Example 1 (comparative Example), a 150 mg tablet including 40 mg oxycodone hydrochloride and no sodium lauryl sulfate was prepared. The composition is shown in Table 1.

TABLE 1

| | | | | pure oxy | |
| | | Adjusted | Adjusted | HCl (Mw = | |
| | Target | amounts | amounts | 351.82 g/mol) | Formulation |
| Ingredient | mg/unit | mg/unit | % by weight | % by weight | (g/batch) |
|---|---|---|---|---|---|
| Oxycodone HCl[1] | 40.0[2] | 42.3[3] | 28.2 | 26.7 | 21.160 |
| Polyethylene Oxide (Polyox WSR-301 NF) | ad 150.0 | 106.2 | 70.8 | | 53.090 |
| Magnesium Stearate | 1.5 | 1.5 | 1.0 | | 0.750 |
| Total | 150.0 | 150.0 | 100.0 | | 75.000 |

[1]According to the certificate of analysis, the oxycodone HCl material used has a water content of 5.2% + residual solvent 0.08% + total impurities 0.2%, which sums up to 5.48 (weight-)% in total. Based thereon, an adjustment factor can be calculated as follows: 100% − 5.48% = 94.52%.
[2]target mg/unit of pure oxycodone HCl (Mw = 351.82 g/mol)
[3]amount of oxycodone HCl material (mg/unit) to be actually used to reach target mg/unit of pure oxycodone HCl (Mw = 351.82 g/mol), calculated by applying the adjustment factor.

The processing steps to manufacture the tablets of Example 1 were as follows:
1. The polyethylene oxide (Polyox WSR-301 NF, screened through a 60-mesh screen, wherein polyethylene oxide that passed through the screen corresponding to the FP material was used, and the material remaining on the 60-mesh screen was discarded) was filled into a 250 mL amber glass bottle;
2. The oxycodone hydrochloride (screened through a 30-mesh screen) was added;
3. The step 2 materials were filled into a 2-liter Bachofen Turbula® mixer and blended for 5 minutes at 70 rpm;
4. The magnesium stearate (screened through a 30-mesh screen) was added to the step 3 blend;
5. The step 4 materials were blended in the Turbula® mixer for 1 minute at 70 rpm;
6. The step 5 blend was compressed to target weight on a single station Manesty Type F3 tablet press using 9/32 inch round, standard concave tooling; and
7. A portion of the step 6 tablets was placed on a mesh screen and cured in a preheated gravity-flow convection oven at a temperature of approximately 72° C. for 30, 60, 120 or 240 minutes (as indicated). Another portion of the step 6 tablets remained uncured.

The upper punch penetration setting of the tablet press, and the results of the measurements of average tablet weight, thickness, breaking strength, and cracking force are indicated in Table 1a). The results of the in-vitro dissolution testing are indicated in Table 1b).

TABLE 1a)

|  | Example 1 | Note |
|---|---|---|
| Upper punch penetration setting (dial/lever) | 25 | start/end |
| Average tablet weight (uncured tablet) [mg] | 154.2 | n = 10 (start/end) |
| Thickness (uncured tablet) [mm] | 4.21 | n = 10 (start/end) |
| Breaking strength (uncured tablet) [Kp]/[N]$^1$ | 12.7/124.5 | n = 10 (start/end) |
| Breaking strength (30 minutes cured tablet) [Kp]/[N]$^1$ | overload$^2$ | n = 3 |
| Cracking force (uncured tablet) [N] | 119 | n = 3 |
| Cracking force (30 minutes cured tablet) [N] | 220 | n = 3 |
| Cracking force (60 minutes cured tablet) [N] | 235 | n = 3 |
| Cracking force (120 minutes cured tablet) [N] | 253 | n = 3 |
| Cracking force (240 minutes cured tablet) [N] | 284 | n = 3 |

$^1$ Kp = 9.807 Newton
$^2$The tablets were deformed, but did not break when subjected to the maximum force of 400N.

TABLE 1b)

In-vitro dissolution results for Example 1

| | % oxycodone hydrochloride released | |
|---|---|---|
| Dissolution time [hours] | Ex. 1 (uncured) (n = 4) | Ex. 1 (30 min. cured) (n = 4) |
| 0.5 | 17 | 17 |
| 1 | 27 | 27 |
| 2 | 44 | 44 |
| 4 | 70 | 71 |
| 8 | 98 | 98 |
| 12 | 105 | 104 |
| 18 | 106 | 105 |

Examples 2-4

In Examples to 4, three different tablets including 40 mg or 10 mg oxycodone hydrochloride and 30 mg sodium lauryl sulfate were prepared. The compositions are shown in Tables 2 to below.

TABLE 2

Composition of Example 2:

| Ingredient | Target mg/unit | Adjusted amounts mg/unit | Adjusted amounts % by weight | pure oxy HCl (Mw = 351.82 g/mol) % by weight | Formulation (g/batch) |
|---|---|---|---|---|---|
| Oxycodone HCl$^1$ | 40.0$^2$ | 42.3$^3$ | 28.2 | 26.7 | 21.160 |
| Polyethylene Oxide (Polyox WSR-301 NF) | ad 150.0 | 76.2 | 50.8 | | 38.090 |
| Sodium Lauryl Sulfate | 30.0 | 30.0 | 20.0 | | 15.000 |
| Magnesium Stearate | 1.5 | 1.5 | 1.0 | | 0.750 |
| Total | 150.0 | 150.0 | 100.0 | | 75.000 |

TABLE 3

Composition of Example 3

| Ingredient | Target mg/unit | Adjusted amounts mg/unit | Adjusted amounts % by weight | pure oxy HCl (Mw = 351.82 g/mol) % by weight | Formulation (g/batch) |
|---|---|---|---|---|---|
| Oxycodone HCl[1] | 40.00[2] | 42.32[3] | 23.2 | 21.9 | 17.633 |
| Polyethylene Oxide (Polyox WSR-301 NF) | ad 182.32 | 108.50 | 59.5 | | 45.208 |
| Sodium Lauryl Sulfate | 30.00 | 30.00 | 16.5 | | 12.500 |
| Magnesium Stearate | 1.50 | 1.50 | 0.8 | | 0.625 |
| Total | 182.32 | 182.32 | 100.0 | | 75.966 |

TABLE 4

Composition of Example 4:

| Ingredient | Target mg/unit | Adjusted amounts mg/unit | Adjusted amounts % by weight | pure oxy HCl (Mw = 351.82 g/mol) % by weight | Formulation (g/batch) |
|---|---|---|---|---|---|
| Oxycodone HCl[1] | 10.0[2] | 10.6[3] | 7.1 | 6.7 | 5.290 |
| Polyethylene Oxide (Polyox WSR-301 NF) | ad 150.0 | 107.9 | 71.9 | | 53.960 |
| Sodium Lauryl Sulfate | 30.0 | 30.0 | 20.0 | | 15.000 |
| Magnesium Stearate | 1.5 | 1.5 | 1.0 | | 0.750 |
| Total | 150.0 | 150.0 | 100.0 | | 75.000 |

The processing steps to manufacture the tablets of Examples 2 to 4 were as follows:
1. The polyethylene oxide (Polyox WSR-301 NF, screened through a 60-mesh screen, wherein polyethylene oxide that passed through the screen corresponding to the FP material was used, and the material remaining on the 60-mesh screen was discarded) was filled into a 250 mL amber glass bottle;

Footnotes for Tables 2-4:
[1] According to the certificate of analysis, the oxycodone HC1 material used has a water content of 5.2%+residual solvent 0.08%+total impurities 0.2%, which sums up to 5.48 (weight-)% in total. Based thereon, an adjustment factor can be calculated as follows: 100%−5.48%=94.52%.
[2] target mg/unit of pure oxycodone HC1 (Mw=351.82 g/mol)
[3] amount of oxycodone HC1 material (mg/unit) to be actually used to reach target mg/unit of pure oxycodone HC1 (Mw=351.82 g/mol), calculated by applying the adjustment factor.

2. The oxycodone hydrochloride (screened through a 30-mesh screen) was added;
3. The sodium lauryl sulfate (screened through a 30-mesh screen) was also added;
4. The step 3 materials were filled into a 2-liter Bachofen Turbula® mixer and blended for 5 minutes at 70 rpm;
5. The magnesium stearate (screened through a 30-mesh screen) was added to the step 4 blend;
6. The step 5 materials were blended in the Turbula® mixer for 1 minute at 70 rpm;
7. The step 6 blend was compressed to target weight on a single station Manesty Type F3 tablet press using 9/32 inch round, standard concave tooling; and
8. A portion of the step 7 tablets was placed on a mesh screen and cured in a preheated gravity-flow convection oven at a temperature of approximately 72° C. for 30, 60, 120 or 240 minutes (as indicated). Another portion of the step 7 tablets remained uncured.

For Examples 2 to 4, the molar ratio of the sodium lauryl sulfate to the oxycodone hydrochloride (Mw=351.82 g/mol), the upper punch penetration setting of the tablet press, and the results of the measurements of average tablet weight, thickness, breaking strength, and cracking force, are indicated in Table 2a). The results of the in-vitro dissolution testing are indicated in Tables 2b), 3a) and 4a).

TABLE 2a)

| | Ex. 2 | Ex. 3 | Ex. 4 | Note |
|---|---|---|---|---|
| Molar ratio SLS/oxycodone HCl (Mw = 351.82 g/mol) | 0.92 | 0.92 | 3.66 | |
| Upper punch penetration setting of the tablet press (dial/lever) | 26 | 28 | 24 | start/end |
| Average tablet weight (uncured tablet) [mg] | 153.6 | 183.4 | 150.4 | n = 10 (start/end) |
| Thickness (uncured tablet) [mm] | 4.17 | 4.86 | 4.19 | n = 10 (start/end) |
| Breaking strength (uncured tablet) [Kp]/[N][1] | 6.4/62.8 | 8.8/86.3 | 8.6/84.3 | n = 10 (start/end) |
| Breaking strength (30 minutes cured tablet) [Kp]/[N][1] | 8.7/85.3 | 15.2/149.1 | overload[2] | n = 3 |
| Cracking force (uncured tablet) [N] | 49 | 67 | 70 | n = 3 |
| Cracking force (30 minutes cured tablet) [N] | 62 | 100 | 154 | n = 3 |
| Cracking force (60 minutes cured tablet) [N] | 65 | 104 | 128 | n = 3 |

TABLE 2a)-continued

|  | Ex. 2 | Ex. 3 | Ex. 4 | Note |
|---|---|---|---|---|
| Cracking force (120 minutes cured tablet) [N] | 68 | 100 | 156 | n = 3 |
| Cracking force (240 minutes cured tablet) [N] | 69 | 109 | 144 | n = 3 |

[1] 1 Kp = 9.807 Newton

[2] The tablets were deformed, but did not break when subjected to the maximum force of 400N.

TABLE 2b)

In vitro dissolution results for Example 2

% oxycodone hydrochloride released

| Dissolution time [hours] | Example 2 (uncured) (n = 4) | Example 2 (30 min. cured) (n = 4) | Example 2 (240 min. cured) (n = 3) |
|---|---|---|---|
| 0.5 | 8 | 7 | 9 |
| 1 | 13 | 13 | 15 |
| 2 | 22 | 21 | 27 |
| 4 | 38 | 38 | 51 |
| 8 | 72 | 73 | 95 |
| 12 | 102 | 102 | 104 |
| 18 | 103 | 103 | 103 |

TABLE 3a)

In vitro dissolution results for Example 3

% oxycodone hydrochloride released

| Dissolution time [hours] | Example 3 (uncured) (n = 4) | Example 3 (30 min. cured) (n = 4) |
|---|---|---|
| 0.5 | 7 | 7 |
| 1 | 11 | 11 |
| 2 | 19 | 19 |
| 4 | 33 | 33 |
| 8 | 60 | 61 |
| 12 | 89 | 91 |
| 18 | 102 | 102 |

TABLE 4a)

In vitro dissolution results for Example 4:

% oxycodone hydrochloride released

| Dissolution time [hours] | Example 4 (uncured) (n = 4) | Example 4 (30 min. cured) (n = 4) |
|---|---|---|
| 0.5 | 5 | 5 |
| 1 | 7 | 7 |
| 2 | 13 | 13 |
| 4 | 23 | 23 |
| 8 | 43 | 44 |
| 12 | 61 | 62 |
| 18 | 80 | 83 |

Example 5

In Example 5, a 250 mg tablet including 40 mg oxycodone hydrochloride and 30 mg sodium lauryl sulfate was prepared. The composition is shown in Table 5 below.

TABLE 5

Composition of Example 5

| Ingredient | Target mg/unit | Adjusted amounts mg/unit | Adjusted amounts % by weight | pure oxy HCl (Mw = 351.82 g/mol) % by weight | Formulation (g/batch) |
|---|---|---|---|---|---|
| Oxycodone HCl[1] | 40.0[2] | 42.3[3] | 16.9 | 16.0 | 16.930 |
| Polyethylene Oxide (Polyox WSRN-12K NF) | ad 250.0 | 176.2 | 70.5 |  | 70.470 |
| Sodium Lauryl Sulfate | 30.0 | 30.0 | 12.0 |  | 12.000 |
| Magnesium Stearate | 1.5 | 1.5 | 0.6 |  | 0.600 |
| Total | 250.0 | 250.0 | 100.0 |  | 100.000 |

[1] According to the certificate of analysis, the oxycodone HCl material used has a water content of 5.2% + residual solvent 0.08% + total impurities 0.2%, which sums up to 5.48 (weight-)% in total. Based thereon, an adjustment factor can be calculated as follows: 100% − 5.48% = 94.52%.
[2] target mg/unit of pure oxycodone HCl (Mw = 351.82 g/mol)
[3] amount of oxycodone HCl material (mg/unit) to be actually used to reach target mg/unit of pure oxycodone HCl (Mw = 351.82 g/mol), calculated by applying the adjustment factor.

The processing steps to manufacture the tablets of Example 5 were as follows:
1. The polyethylene oxide (Polyox WSR N-12K NF, screened through a 60-mesh screen, wherein polyethylene oxide that passed through the screen corresponding to the FP material was used, and the material remaining on the 60-mesh screen was discarded) was filled into a 500 mL amber glass bottle;
2. The oxycodone hydrochloride (screened through a 30-mesh screen) was added;
3. The sodium lauryl sulfate (screened through a 30-mesh screen) was also added;

4. The step 3 materials were filled into a 2-liter Bachofen Turbula® mixer and blended for 5 minutes at 70 rpm;
5. The magnesium stearate (screened through a 30-mesh screen) was added to the step 4 blend;
6. The step 5 materials were blended in the Turbula® mixer for 1 minute at 70 rpm;
7. The step 6 blend was compressed to target weight on a single station Manesty Type F3 tablet press using 11/32 inch round, standard concave tooling; and
8. A portion of the step 7 tablets was placed on a mesh screen and cured in a preheated gravity-flow convection oven at a temperature of 70-72° C. for 30 minutes. Another portion of the step 7 tablets remained uncured.

The molar ratio of the sodium lauryl sulfate to the oxycodone hydrochloride (Mw=351.82 g/mol), the upper punch penetration setting of the tablet press, and the results of the measurements of average tablet weight, thickness, breaking strength, and cracking force, are indicated in Table 5a). The results of the in vitro dissolution testing are indicated in Table 5b).

TABLE 5a)

|  | Example 5 | Note |
|---|---|---|
| Molar ratio SLS/oxycodone HCl (Mw = 351.82 g/mol) | 0.92 |  |
| Upper punch penetration setting of the tablet press (dial/lever) | 24 | start/end |
| Average tablet weight (uncured tablet) [mg] | 252.0 | n = 10 (start/end) |
| Thickness (uncured tablet) [mm] | 4.71 | n = 10 (start/end) |
| Breaking strength (uncured tablet) [Kp]/[N][1] | 8.1/79.4 | n = 10 (start/end) |
| Breaking strength (30 minutes cured tablet) [Kp]/[N][1] | overload[2] | n = 3 |
| Cracking force (uncured tablet) [N] | 78 | n = 3 |
| Cracking force (30 minutes cured tablet) [N]] | 162 | n = 3 |

[1] 1 Kp = 9.807 Newton
[2] The tablets were deformed, but did not break when subjected to the maximum force of 400N.

TABLE 5b)

In vitro dissolution results for Example 5

| Dissolution time [hours] | % oxycodone hydrochloride released Ex. 1 (30 min. cured) (n = 3) |
|---|---|
| 0.5 | 8 |
| 1 | 14 |
| 2 | 26 |
| 4 | 51 |
| 8 | 95 |
| 12 | 101 |

The invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference for all purposes.

What is claimed is:

1. A solid oral extended release pharmaceutical dosage form comprising an extended release matrix formulation, the extended release matrix formulation comprising:
   (1) at least one active agent salt comprising a cationic active agent molecule and an anionic counterion, wherein the at least one active agent salt comprises oxycodone hydrochloride;
   (2) about 15% by weight to about 25% by weight (based on the weight of the extended release matrix formulation) of at least one anionic surfactant comprising sodium lauryl sulfate, potassium lauryl sulfate, ammonium lauryl sulfate, ethanolammonium lauryl sulfate, diethanolammonium lauryl sulfate, and triethanolammonium lauryl sulfate or mixtures thereof, wherein the molar ratio of the at least one anionic surfactant to the at least one active agent salt is from about 1:2 to about 10:1; and
   (3) at least about 40% by weight (based on the weight of the extended release matrix formulation) of at least one polyethylene oxide;
   wherein the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with an amount of the at least one active agent released at x hours, wherein x is an integer selected from a number between 2 and 12; and
   an amount of the at least one active agent released at y hours, wherein y is an integer selected from a number between 6 and 24, and y≥x+4;
   which complies at least for one combination of x and y with equations (I) and (II):
   the amount released at y hours≤(y/x×amount released at x hours)×1.25 (I),
   the amount released at y hours≥(y/x×amount released at x hours)×0.75 (II),
   wherein the dosage form is free of core-shell particulates.

2. The solid oral extended release pharmaceutical dosage form of claim 1, wherein the molar ratio of the at least one anionic surfactant to the at least one active agent is from about 2:1 to about 8:1.

3. The solid oral extended release pharmaceutical dosage form of claim 1, wherein the molar ratio of the at least one anionic surfactant to the at least one active agent salt is from about 2:1 to about 5:1.

4. The solid oral extended release pharmaceutical dosage form of claim 1, wherein the molar ratio of the at least one anionic surfactant to the at least one active agent salt is from about 3:1 to about 4:1.

5. The solid oral extended release pharmaceutical dosage form of claim 1, wherein the at least one polyethylene oxide has, based on rheological measurements, an approximate molecular weight of from 900,000 to 8,000,000.

6. The solid oral extended release pharmaceutical dosage form of claim 1, wherein the at least one polyethylene oxide has, based on rheological measurements, an approximate molecular weight of from 4,000,000 to 8,000,000.

7. The solid oral extended release pharmaceutical dosage form of claim 1, wherein the extended release matrix formulation comprises from about 50% by weight to about 90% by weight (based on the weight of the extended release matrix formulation) of said at least one polyethylene oxide.

8. The solid oral extended release pharmaceutical dosage form of claim 1, wherein the at least one anionic surfactant is sodium lauryl sulfate.

9. The solid oral extended release pharmaceutical dosage form of claim 1, wherein the extended release matrix formulation comprises from about 5% by weight to about 25% by weight (based on the weight of the extended release matrix formulation) of said at least one anionic surfactant.

10. The solid oral extended release pharmaceutical dosage form of claim 1, wherein the extended release matrix formulation comprises from about 0.5% by weight to about 5% by weight (based on the weight of the extended release matrix formulation) of a lubricant.

11. A process of preparing a solid oral extended release pharmaceutical dosage form, comprising the steps of
(a) combining at least
  (1) at least one active agent salt comprising a cationic active agent molecule and an anionic counterion, wherein the at least one active agent salt comprises oxycodone hydrochloride;
  (2) about 15% by weight to about 25% by weight (based on the weight of the extended release matrix formulation) of at least one anionic surfactant comprising sodium lauryl sulfate, potassium lauryl sulfate, ammonium lauryl sulfate, ethanolammonium lauryl sulfate, diethanolammonium lauryl sulfate, and triethanolammonium lauryl sulfate or mixtures thereof, wherein the molar ratio of the at least one anionic surfactant to the at least one active agent salt is from about 1:2 to about 10:1; and
  (3) at least about 40% by weight (based on the weight of the extended release matrix formulation) of at least one polyethylene oxide;
to form a composition;
(b) shaping the composition to form an extended release matrix formulation; and
(c) optionally curing said extended release matrix formulation comprising at least a curing step of subjecting the extended release matrix formulation to a temperature which is at least the softening temperature of said polyethylene oxide for a time period of at least about 1 minute;
wherein the dosage form, when subjected to an in-vitro dissolution test in a USP Apparatus 1 (basket) at 100 rpm in 900 ml simulated gastric fluid without enzymes (SGF) at 37.0±0.5° C., provides a dissolution rate with
an amount of the at least one active agent released at x hours, wherein x is an integer selected from a number between 2 and 12; and
an amount of the at least one active agent released at y hours, wherein y is an integer selected from a number between 6 and 24, and y≥x+4;
which complies at least for one combination of x and y with equations (I) and (II):
the amount released at y hours≤(y/x×amount released at x hours)×1.25 (I),
the amount released at y hours≥(y/x×amount released at x hours)×0.75 (II).

12. A method of treating or preventing pain comprising administering to a patient identified in need thereof a solid oral extended release pharmaceutical dosage form of claim 1, wherein the at least one active agent comprises an opioid agonist, and said opioid agent is present in an analgesically effective amount.

* * * * *